United States Patent
Bansal et al.

(10) Patent No.: US 11,897,785 B2
(45) Date of Patent: Feb. 13, 2024

(54) METHOD FOR PREPARING AN AQUEOUS DISPERSION OF METAL OXIDE PARTICLES

(71) Applicant: Royal Melbourne Institute of Technology, Melbourne (AU)

(72) Inventors: Vipul Bansal, Heidelberg West (AU); Mandeep Singh, South Morang (AU); Rajesh Ramanathan, Malvern East (AU); Amanda Anderson, Eltham (AU)

(73) Assignee: Royal Melbourne Institute of Technology, Melbourne (AU)

( * ) Notice: Subject to any disclaimer, the term of this patent is extended or adjusted under 35 U.S.C. 154(b) by 680 days.

(21) Appl. No.: 17/057,626

(22) PCT Filed: May 22, 2019

(86) PCT No.: PCT/AU2019/050500
§ 371 (c)(1),
(2) Date: Nov. 20, 2020

(87) PCT Pub. No.: WO2019/222803
PCT Pub. Date: Nov. 28, 2019

(65) Prior Publication Data
US 2021/0163311 A1    Jun. 3, 2021

(30) Foreign Application Priority Data
May 22, 2018   (AU) ............................... 2018901786

(51) Int. Cl.
*A61K 41/00*    (2020.01)
*A61K 49/18*    (2006.01)
(Continued)

(52) U.S. Cl.
CPC ...... *C01G 49/0009* (2013.01); *A61K 41/0052* (2013.01); *A61K 49/1839* (2013.01);
(Continued)

(58) Field of Classification Search
CPC .... C01G 49/0009; C01G 49/06; C01G 49/08; C01G 99/00; C01G 1/00; C01P 2006/22;
(Continued)

(56) References Cited

U.S. PATENT DOCUMENTS
2014/0087211 A1    3/2014   Omura

FOREIGN PATENT DOCUMENTS
DE          39 08 014 A1      9/1989
DE     10 2007042862 A1 *   3/2009   ............. C11D 3/168
(Continued)

OTHER PUBLICATIONS

Jing Cai et al. "Large-Scale, Facile Transfer of Oleic Acid-Stabilized Iron Oxide Nanoparticles to the Aqueous Phase for Biological Applications" Langmuir, vol. 33, pp. 1662-1669 (2017). (Year: 2017).*
(Continued)

*Primary Examiner* — Timothy C Vanoy
(74) *Attorney, Agent, or Firm* — Wolf, Greenfield & Sacks, P.C.

(57) ABSTRACT

A method for preparing an aqueous dispersion of metal oxide particles is disclosed. The method comprises the step of performing phase transfer of a plurality of metal oxide particles capped with hydrophobic ligands on a surface there of by contacting the metal oxide particles with a combination of tertiary amine and water to form a biphasic mixture, and agitating said biphasic mixture to produce an aqueous dispersion of metal oxide particles capped with hydrophobic ligands and tertiary amine ligands on the surface thereof.

18 Claims, 12 Drawing Sheets

(51) Int. Cl.
  *C01G 49/00* (2006.01)
  *C01G 49/06* (2006.01)
  *C01G 49/08* (2006.01)

(52) U.S. Cl.
  CPC .......... *A61K 49/1851* (2013.01); *C01G 49/06* (2013.01); *C01G 49/08* (2013.01); *C01P 2006/22* (2013.01); *C01P 2006/42* (2013.01)

(58) Field of Classification Search
  CPC ............. C01P 2006/42; A61K 41/0052; A61K 49/1839; A61K 49/1851; A61K 49/1806
  See application file for complete search history.

(56) References Cited

FOREIGN PATENT DOCUMENTS

| WO | WO 2017 015 150 A1 * | 1/2017 | ............. A61K 49/00 |
|----|----------------------|--------|--------------------------|
| WO | WO 2018/049468 A1    | 3/2018 |                          |

OTHER PUBLICATIONS

Extended European Search Report for European Application No. 19807310.8, dated Feb. 2, 2022.
International Search Report and Written Opinion for International Application No. PCT/AU2019/050500, dated Aug. 2, 2019.
International Preliminary Report on Patentability for International Application No. PCT/AU2019/050500, dated Dec. 2, 2020.
Bloeman et al., Improved functionalization of oleic acid-coated iron oxide nanoparticles for biomedical applications. Journal of Nanoparticle Research. Sep. 1, 2012;14(9):1100.
Singh, Triethylamine: a versatile ligand to control the properties of nanomaterials. RMIT University Thesis. Jan. 2019:1-198.
Zhao et al., Preparation and reversible phase transfer of $CoFe_2O_4$ nanoparticles. The Journal of Physical Chemistry C. Jun. 7, 2007;111(22):7875-8.

* cited by examiner

METHOD FOR PREPARING AN AQUEOUS DISPERSION OF METAL OXIDE PARTICLES

RELATED APPLICATIONS

This Application is a national stage filing under 35 U.S.C. § 371 of International Patent Application Serial No. PCT/AU2019/050500, filed May 22, 2019, which claims priority to Australian application number 2018901786, filed May 22, 2018. The entire contents of these applications are incorporated herein by reference in their entirety.

TECHNICAL FIELD

The present invention relates to a method for preparing an aqueous dispersion of metal oxide particles, and more particularly, iron oxide particles, and uses thereof.

The invention has been developed primarily for use in preparing an aqueous dispersion of iron oxide particles for use in various applications involving magnetism mediated processes, and in particular, for use in magnetic hyperthermia treatment, and will be described hereinafter with reference to this application. However, it will be appreciated that the invention is not limited to this particular field of use.

The following discussion of the background to the invention is intended to facilitate an understanding of the invention. However, it should be appreciated that the discussion is not an acknowledgement or admission that any of the material referred to was published, known or part of the common general knowledge in Australia or any other country as at the priority date of any one of the claims of this specification.

BACKGROUND OF INVENTION

Nanomaterials (nano- and micro-particles) have a variety of applications, and these applications mostly depend on whether these particles are dispersible in an organic solvent or an aqueous solvent. For example, iron oxide particles are promising magnetic materials for biomedical applications due to the high biocompatibility of magnetite ($Fe_3O_4$) and maghemite ($\gamma$-$Fe_2O_3$). These particles have found use in a variety of applications ranging from magnetic resonance imaging (MRI), magnetic particle imaging (MPI), hyperthermal treatment of cancer, biosensing, magnetic memories, magnetic separation of important chemicals and biochemicals, as well as environmental remediation.

A vast majority of these applications require these iron oxide particles to be dispersed in aqueous solutions. However, most of the scalable synthesis routes for producing high quality iron oxide particles are only possible in organic solvents.

For instance, the use of thermal decomposition methods for the synthesis of iron oxide particles with ligands such as oleic acid coated on the particle surface, offers good control over nanoparticle size, morphology and other physico-chemical properties, but the resultant particles are heavily coated with a thick layer of oleic acid and/or other high boiling surfactants. These coatings not only adversely affect magnetic properties; they also pose challenges in employing these high quality superparamagnetic iron oxide nanoparticles (SPIONs) for biomedical applications due to their poor aqueous dispersibility. Considering the high quality of these oleic acid-capped SPIONs, efforts have been made to make them water dispersible through ligand exchange, ligand modification, silanization and surfactant/polymer coatings. However, these additional surface coatings have consistently resulted in lower magnetisation over the parent particles due to the contributions from number of factors, like aggregation, increase in magnetic dead layer, magnetic phase change, etc. Overall, the improvement in the magnetic properties of SPIONs after their aqueous phase transfer has remained challenging, yet highly desirable from the perspective of biomedical applications.

As such, for clinical applications, access to better quality SPIONs that offer longer sedimentation times, high surface area, high net magnetization, and smaller magnetic dipole interactions continues to remain in high demand. One potential application of such SPIONs is in remote controlled magnetic hyperthermia; wherein SPIONs can be used as localised heat generators to, for instance, destroy malignant tumours in the presence of an external alternating magnetic (AC) field. Exposing SPIONs to a high frequency AC field can generate localised heat either due to rotation of the entire magnetic particle within the surrounding fluid (Brownian relaxation, $T_B$) and/or due to the rotation of the magnetic moment within the magnetic core (Néel relaxation, $T_N$). It is extremely challenging to determine the exact contribution of each of these relaxations to the net heat generated by the SPIONs and only a selected few studies have been able to distinguish relative contributions of these relaxations.

Yet another potential application of improved quality SPIONs is magnetic particle imaging (MPI); an emerging non-invasive tomographic technique that directly detects superparamagnetic nanoparticles, such as SPIONs. MPI has potential applications in diagnostic imaging and therapeutic treatment. This technique is advantageously high resolution and high contrast over fast timescales. Additionally, it is radiation free.

Given the above, particles produced in organic solvents are not dispersible in aqueous solvents, and therefore, may not be suitable for many such applications, particularly biological and clinical applications.

The same restrictions apply to many other particles and therefore, there is a strong need to develop efficient routes for the phase transfer of iron oxide and other inorganic particles from an organic phase to an aqueous phase. Efficiency in this context means a method that is rapid, low-cost, and/or commercially/environmentally sustainable, and that does not significantly influence the biocompatibility and other physico-chemical properties of the original material after phase transfer.

The literature based protocols for achieving the phase-transfer of particles typically employ bulky surfactant molecules or coat the original material with another inorganic material, such as silica. These protocols significantly change the original properties of the material, making them undesirable for the intended applications.

Another desirable property of efficient phase-transfer protocols is that the particles obtained after phase transfer should be well dispersed in the new aqueous solvent and should not aggregate into bigger particles. If aggregation occurs, the particles may again lose their desirable application-focussed properties and functionalities.

The present invention seeks to provide a method for preparing an aqueous dispersion of metal oxide particles, and uses thereof, which will overcome or substantially ameliorate at least some of the deficiencies of the prior art, or to at least provide an alternative.

SUMMARY OF INVENTION

According to a first aspect of the present invention, there is provided a method for preparing an aqueous dispersion of metal oxide particles, comprising the step of: performing phase transfer of a plurality of metal oxide particles capped with hydrophobic ligands on a surface there of by contacting the metal oxide particles with a combination of tertiary amine and water to form a biphasic mixture, and agitating said biphasic mixture to produce an aqueous dispersion of metal oxide particles capped with hydrophobic ligands and tertiary amine ligands on the surface thereof.

In one embodiment, the biphasic mixture is agitated by sonicating the biphasic mixture for greater than 5 minutes.

In one embodiment, the metal oxide particles capped with hydrophobic ligands and tertiary amine ligands on the surface there of migrate from the biphasic mixture into the aqueous phase upon standing overnight.

In one embodiment, prior to the phase transfer step, the method further comprises the step of: dissolving the tertiary amine in a solvent to form a solution of the tertiary amine.

In one embodiment, the solvent is a non-polar solvent selected from the group consisting of hexane, toluene and a combination thereof.

In one embodiment, the solvent is a polar solvent selected from the group consisting of water, methanol, ethanol, propanol, an ether, chloroform, dimethyl formamide (DMF), dimethyl sulfoxide (DMSO), and any combination thereof.

In one embodiment, the method further comprises the step of: separating the iron oxide particles capped with hydrophobic ligands and tertiary amine ligands on the surface thereof from the aqueous solution using a physical separation procedure.

In one embodiment, the iron oxide particles capped with hydrophobic ligands and tertiary amine ligands are separated from the biphasic mixture by centrifuging the biphasic mixture at greater than 1000 g for greater than 2 minutes.

In one embodiment, prior to the phase transfer step, the method further comprises the step of: dispersing a plurality of metal oxide particles capped with tertiary amine ligands on a surface thereof in an organic solution of hydrophobic ligands to form a mixture, and agitating said mixture to form a plurality of metal oxide particles capped with hydrophobic ligands on the surface thereof.

Preferably, the hydrophobic ligands are dissolved in an organic solvent selected from the group consisting of acetone, methanol, ethanol, propanol, an ether, chloroform, dimethyl formamide (DMF), dimethyl sulfoxide (DMSO), and any combination thereof.

In one embodiment, the method further comprises the step of: separating the metal oxide particles capped with hydrophobic ligands on the surface thereof from the organic dispersion using a physical separation procedure.

Preferably, the physical separation procedure is selected from the group consisting of magnetic separation, centrifugation, filtration and decantation.

In one embodiment, the plurality of metal oxide particles are iron oxide particles, and prior to the phase transfer step, the method comprises the step of: contacting an aqueous solution of iron (III) and iron (II) ions with a tertiary amine and hydrophobic ligands dissolved in an organic solvent to facilitate hydrolysis of the iron (III) and iron (II) ions to produce an organic dispersion of iron oxide particles capped with hydrophobic ligands on the surface thereof.

Preferably, the iron (III) and iron (II) ions are present in the aqueous solution in a 2:1 molar ratio.

Suitably, the iron (III) ions are provided in the form of $FeCl_3 \cdot 6H_2O$ and the iron (II) ions are provided in the form of $FeCl_2 \cdot 4H_2O$.

Preferably, the organic solvent is miscible with the aqueous solution.

Preferably, the organic solvent is acetone.

In one embodiment, the contacting step is conducted at a temperature that falls within a range of 70° C. to 85° C.

In one embodiment, the method further comprises the step of: washing the iron oxide particles capped with hydrophobic ligands on the surface thereof with a mixture of acetone:methanol in a 1:1 (vol/vol) ratio.

In one embodiment, the tertiary amine is a trialkylamine.

Suitably, the trialkylamine is selected from the group consisting of triethylamine and trimethylamine.

Preferably, the tertiary amine is triethylamine.

In one embodiment, the hydrophobic ligands are selected from the group consisting of an alkanoic acid, a saturated or unsaturated fatty acid, or a combination thereof.

Preferably, the hydrophobic ligands are oleic acid.

Preferably, the metal oxide particles are iron oxide particles.

Preferably, the iron oxide particles are maghemite ($\gamma$-$Fe_2O_3$) and/or magnetite ($Fe_3O_4$).

According to a second aspect of the present invention, there is provided metal oxide particles prepared according to the method of the first aspect.

According to a third aspect of the present invention, there is provided a use of an aqueous dispersion of metal oxide particles produced according to the method of the first aspect as magnetic particles in a magnetism-mediated process selected from the group of processes consisting of magnetic hyperthermia treatment, magnetic labelling, magnetic separation, magnetic resonance imaging, magnetism-directed targeting and magnetism-induced heating.

According to a fourth aspect of the present invention there is provided a composition for use in a magnetism-mediated process comprising an aqueous dispersion of metal oxide particles produced according to the method of the first aspect, the magnetism-mediated process selected from the group of processes consisting of magnetic hyperthermia treatment, magnetic labelling, magnetic separation, magnetic resonance imaging, magnetic particle imaging, magnetism-directed targeting and magnetism-induced heating.

Other aspects of the invention are also disclosed.

BRIEF DESCRIPTION OF DRAWINGS

Notwithstanding any other forms which may fall within the scope of the present invention, preferred embodiments of the invention will now be described, by way of example only, with reference to the accompanying drawings in which.

DETAILED DESCRIPTION

It is to be understood that the following description is for the purpose of describing particular embodiments only and is not intended to be limiting with respect to the above description.

The present invention is predicated on the finding of a method for preparing an aqueous dispersion of metal oxide particles in the form of superparamagnetic iron oxide nanoparticles (SPIONs) that can be used in a multitude of applications, particularly biomedical applications. The method has identified the use of a tertiary amine as a unique agent for mediating the phase transfer of poorly aqueous dispersible hydrophobic ligand capped iron oxide particles to the aqueous phase. This method precludes the need for additional coatings on the SPIONs to render them aqueous dispersible; a strategy which is widely known to have an adverse effect on the magnetic properties of these SPIONs, and thus their efficacy in biomedical applications such as in the treatment of magnetic hyperthermia. Accordingly, particles prepared by the described methods provide an opportunity to fundamentally distinguish the relative contributions of Brownian ($T_B$) and Wel ($T_N$) relaxations with respect to this treatment.

While the embodiments of the present invention described below focus on preparing an aqueous dispersion of iron oxide particles capped with oleic acid molecules, it will be appreciated by persons of ordinary skill in the relevant art that the present invention is not limited to such, and that other metal oxide particles capped with the same or other hydrophobic ligands may fall within the scope of the invention as presently claimed.

[Path A]

Method for Path A

According to a preferred embodiment of the present invention, there is provided a method for preparing an aqueous dispersion of metal oxide particles.

As indicated above, the metal oxide particles used to facilitate an understanding of the preferred embodiments of the present invention, are provided in the form of superparamagnetic iron oxide nanoparticles (SPIONs).

Figure 1:
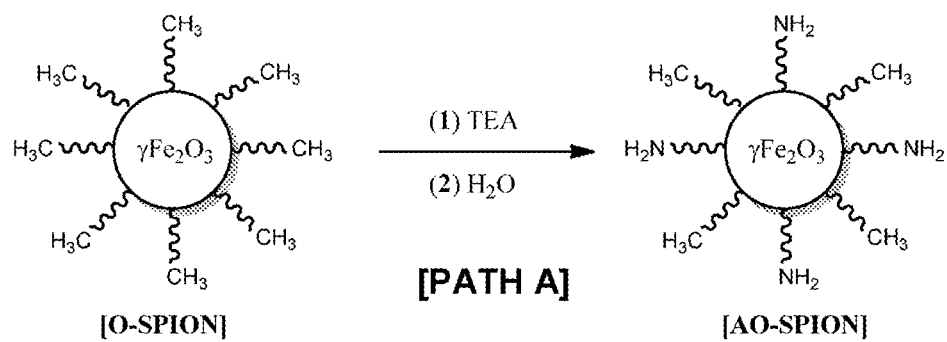
FIG. 1 shows a schematic representation of a method according to a preferred embodiment of the present invention that, when following Path A, includes a triethylamine (TEA)-mediated step for facilitating the phase transfer of oleic acid capped superparamagnetic iron oxide nanoparticles (O-SPIONs) from a non-aqueous phase to an aqueous phase to produce an aqueous dispersion of superparamagnetic iron oxide nanoparticles (SPIONs) capped with both oleic acid and triethylamine ligands (AO-SPIONs)

According to one approach as shown in FIG. 1 (Path A), the method comprises the step of: performing phase transfer of a plurality of superparamagnetic iron oxide nanoparticles (SPIONs) capped with hydrophobic ligands on the surface thereof by contacting the hydrophobic ligand capped SPION particles with a pre-mixed combination of (1) a tertiary amine and (2) water to form a biphasic mixture having an aqueous phase and a non-aqueous phase, and agitating said biphasic mixture to produce an aqueous dispersion of iron oxide particles capped with both hydrophobic ligands and tertiary amine ligands on their surface.

In essence, the tertiary amine is a dynamic amphiphilic ligand that acts in the presence of water to facilitate the rapid and facile phase-transfer of the hydrophobic ligand capped SPIONs from the non-aqueous phase to the aqueous phase.

As will be appreciated by persons of ordinary skill in the relevant art, the order in which the tertiary amine and water are added to the hydrophobic ligand capped SPION particles is not limited to that shown in FIG. 1 (Path A).

For instance, in an alternative approach, the hydrophobic ligand capped SPION particles are first dispersed in an organic medium such as hexane (or toluene) to form a non-aqueous dispersion before adding the pre-mixed combination of tertiary amine and water.

In yet another alternative approach, the hydrophobic ligand capped SPION particles are first dispersed in hexane (or toluene) to form a non-aqueous dispersion, and then water is added to the non-aqueous dispersion before adding the tertiary amine.

In still another alternative approach, the hydrophobic ligand capped SPIONs are first dispersed in hexane (or toluene) to form a non-aqueous dispersion, and then the tertiary amine is added to the non-aqueous dispersion before adding the water.

It will also be appreciated that the tertiary amine is not limited to being used in neat form, but may in fact be dissolved in a non-polar solvent such as hexane or toluene or a polar solvent such as water, methanol or ethanol prior to dispersing the hydrophobic ligand capped SPIONs.

Whichever approach is adopted, it is critical that the hydrophobic ligand capped SPION particles must be exposed to both the tertiary amine and water for this method to work. If the hydrophobic ligand capped SPION particles have not been exposed to either one of these components, then the hydrophobic ligand capped SPION particles will not undergo phase transfer to the aqueous phase.

In terms of the reactants themselves, the inventors have found that the hydrophobic ligands may be selected from the group consisting of an alkanoic acid, a saturated or unsaturated fatty acid, or a combination thereof. While the tertiary amine may be a trialkylamine such as triethylamine.

As shown in the schematic representation in FIG. 1, when following Path A, good results have been demonstrated when the hydrophobic ligands capping the SPIONs are oleic acid (OA) molecules and the tertiary amine used to mediate the phase transfer of these oleic acid capped SPION particles (denoted as O-SPIONs) from the non-aqueous phase to an aqueous phase is triethylamine (TEA).

The inventors believe that under the right conditions, trimethylamine may also prove to be effective as an agent to facilitate the phase transfer step.

The outcome of this TEA-mediated phase transfer is the production of an aqueous dispersion of SPION particles capped with both oleic acid and triethylamine ligands (denoted as AO-SPIONs).

What follows is a description of one particular embodiment of the method illustrated in FIG. 1, when following Path A.

To 1 g of the O-SPION particles is added 40 mL of hexane to form a slurry. The slurry is then shaken to disperse these O-SPION particles in the organic solvent to form a non-aqueous phase. While hexane has been shown to provide good results, it will be appreciated by those skilled in the relevant art that other non-polar solvents such as toluene may be used. In either case, the volume of organic solvent may be varied from 1 mL to 5000 mL, as required.

Next, 40 mL of water is then added to the non-aqueous phase to form a biphasic mixture. The volume of water may be varied from 1 mL to 5000 mL, but need not necessarily be the same as the volume of hexane used.

Then, 1 mL of triethylamine (TEA) is added to this solution in either in (i) neat form, (ii) dissolved in a non-polar solvent such as hexane, toluene or a combination thereof, or (iii) dissolved in a polar solvent such as water, methanol, ethanol, propanol, an ether, chloroform, dimethyl formamide (DMF), dimethyl sulfoxide (DMSO), and any combination thereof. The mixture is then sonicated for greater than 5 minutes to form a biphasic mixture that appears in the form of a milky emulsion. Again, the volume of TEA may be varied from 0.001 mL to 100 mL, as required.

This milky emulsion can either be (i) left standing overnight without disturbing to self-break into separate aqueous and non-aqueous phases to allow the AO-SPION particles to migrate from the emulsion into the aqueous phase, or (ii) centrifuged at greater than 1000 g for about 2 to 10 minutes to rapidly break down the emulsion into the two separate phases (the non-aqueous phase and the aqueous phase) in which the AO-SPION particles are dispersed in the aqueous phase.

Finally, the resultant AO-SPION particles can be collected from the aqueous phase using any one of a selection of physical separation procedures such as centrifugation, magnetic separation, filtration, decantation or solvent evaporation. Once isolated, the AO-SPION particles can then be dried and stored as a powder for future use. The dried powder thus obtained can be readily redispersed in an aqueous solvent as required.

In the case of Path A, the O-SPION particles used were obtained according to the thermal decomposition method described in Park, J., et al., *Nature Materials,* 2004, vol. 3, 891-895[1], and purified according to the procedure described in PCT/AU2017/050981[2], of which both protocols are incorporated herein by reference.

Characterization of SPION Particles Prepared According to Path A

Figure 2:
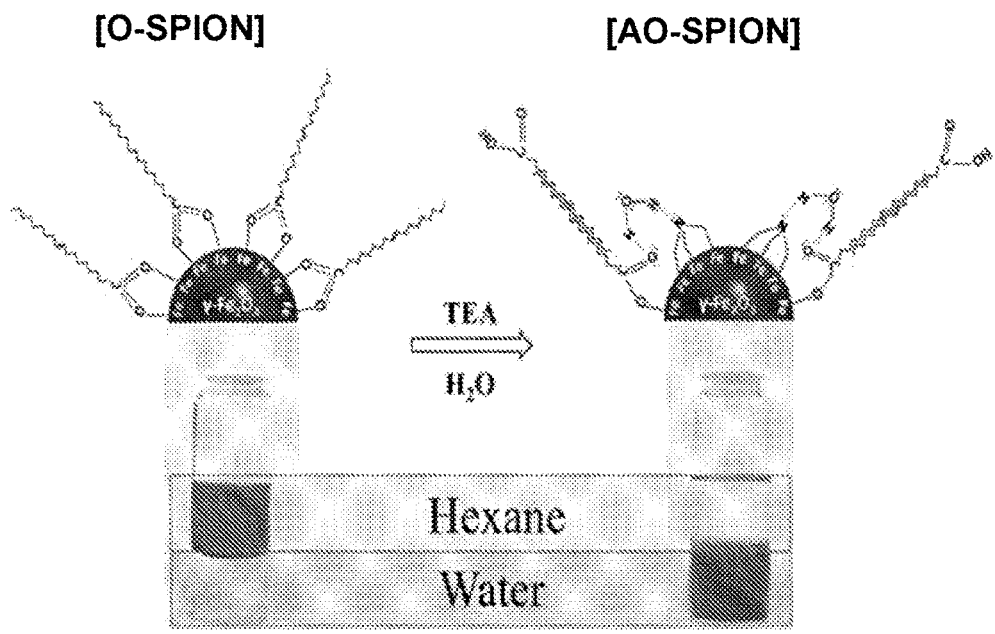
FIG. 2 shows photographs comparing the solubility characteristics of powders of the O-SPION particles (dispersed in hexane) and AO-SPION particles (dispersed in water)

FIG. 2 shows photographs comparing the solubility characteristics of powders of the O-SPION particles (dispersed in hexane) and AO-SPION particles (dispersed in water). Here, is clear from the image of the sample vial shown on the left-hand side that all of the O-SPION particles are present in the non-aqueous phase.

While the image of the sample vial shown on the right-hand side shows that by virtue of the TEA-mediated phase transfer step, all of the O-SPION particles have been phase transferred from the non-aqueous phase to the aqueous phase.

While not wishing to be bound by any one particular theory, the inventors believe that this outcome is due to the fact that when the O-SPION particles (in hexane) undergo the TEA-mediated phase-transfer step in water, some of the bulky oleic acid molecules on the surface of the O-SPION particles are rearranged in their orientation and replaced by the smaller TEA molecules. By virtue of this, the resultant particles have a mixture of oleic acid and triethylamine molecules on the surface of the particles. These dual amine/oleic acid-capped superparamagnetic iron oxide nanoparticles are hereinafter referred to as AO-SPION particles.

Figure 3:
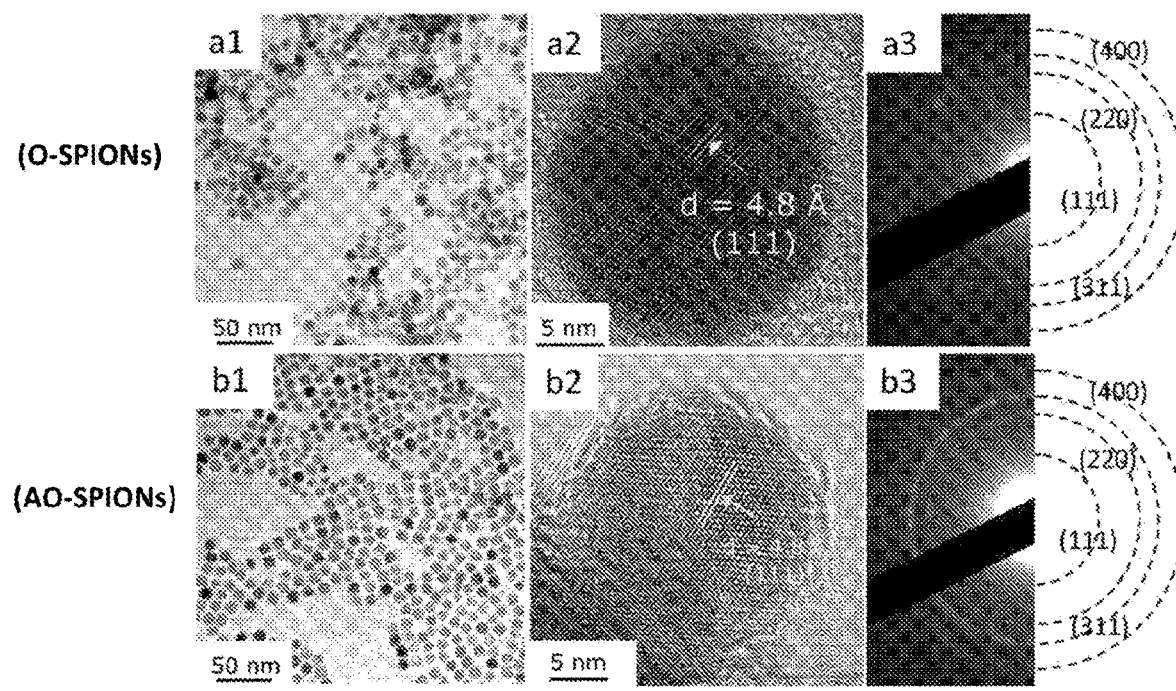
FIG. 3 shows TEM and HRTEM images along with SAED patterns of the O-SPION particles (a1-a3), and AO-SPION particles (b1-b3) produced according to the (TEA)-mediated phase transfer step of the method of FIG. 1.

FIG. 3 shows the transmission electron microscopy (TEM) and high resolution transmission electron microscopy (HRTEM) images, along with the selected area electron diffraction (SAED) patterns of the O-SPION particles (a1-a3), and AO-SPIONs particles (b1-b3) produced according to the (TEA)-mediated phase transfer step of the method of FIG. 1 (Path A).

Overall, this data shown in this figure confirms that the morphological and crystal quality of the particles have not changed during the TEA-mediated phase transfer method into the aqueous phase. Indeed, the d-spacings and lattice planes in images a2, a3, b2 and b3 confirm that both the O-SPION and AO-SPION particles are high quality single-crystals of maghemite ($\gamma$-$Fe_2O_3$).

Figure 4:
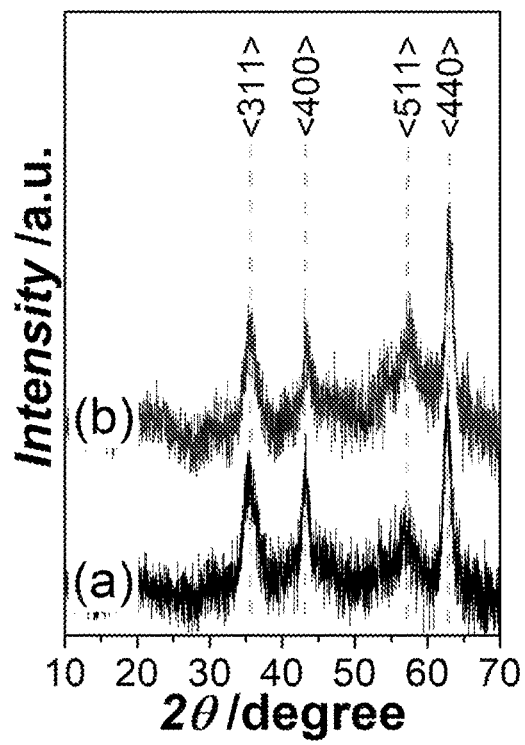
FIG. 4 shows X-ray diffraction (XRD) patterns of (a) the O-SPION particles, and (b) the AO-SPION particles produced according to the (TEA)-mediated phase transfer step of the method of FIG. 1.

FIG. 4 shows X-ray diffraction (XRD) patterns of (a) the O-SPION particles, and (b) the AO-SPION particles produced according to the (TEA)-mediated phase transfer step of the method of FIG. 1 (Path A).

The X-ray diffraction data of the AO-SPION particles confirms that these particles are composed of maghemite ($\gamma$-$Fe_2O_3$) and their structure does not change during the TEA-mediated phase transfer step.

Figure 5:
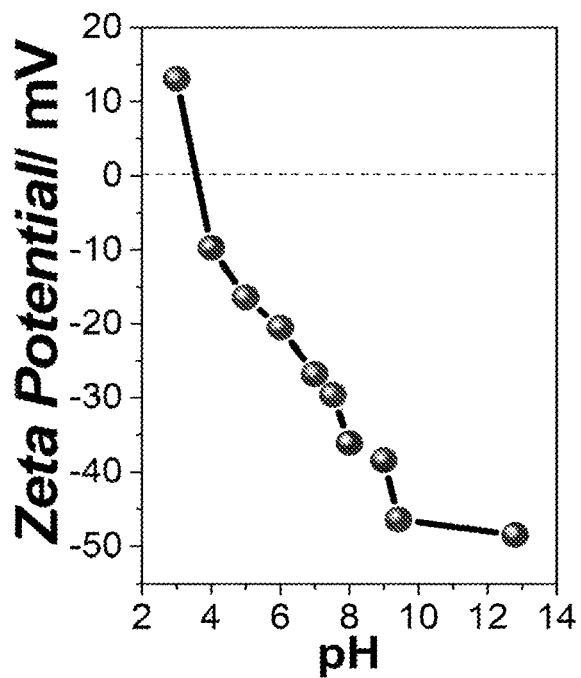
FIG. 5 provides a plot showing the zeta potential of the AO-SPION particles produced according to the (TEA)-mediated phase transfer step of the method of FIG. 1, when measured at different pH values.

FIG. 5 provides a plot showing the zeta potential of the AO-SPION particles produced according to the (TEA)-mediated phase transfer step of the method of FIG. 1 (Path A), when measured at different pH values.

The high zeta potential values (irrespective of charge) suggest that these aqueous phase transferred particles remain highly stable across a variety of pH values. The particle surface is negatively charged at pH values equal to or higher than 4, but they can be switched to be a positively charged surface at pH values equal to or less than 3. In either case, these AO-SPION particles have high zeta-potential, suggesting their high colloidal stability through electrostatic charge repulsion mechanisms.

Figure 6:
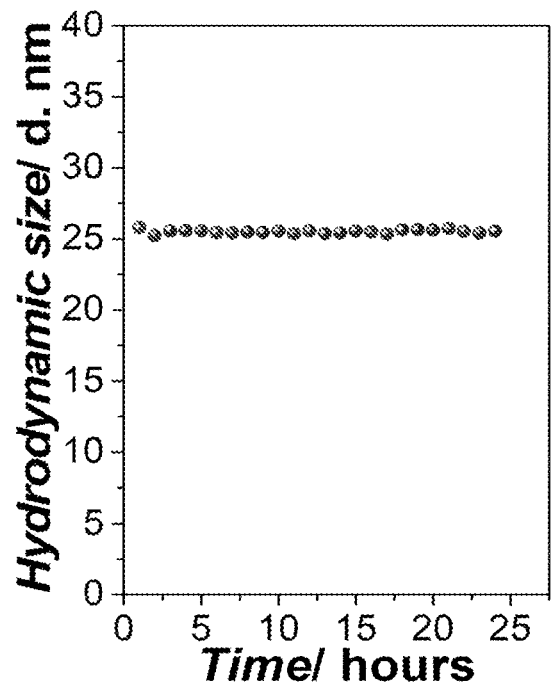
FIG. 6 provides a plot showing the variance in hydrodynamic size of the AO-SPION particles produced according to the (TEA)-mediated phase transfer step of the method of FIG. 1, when measured over time without disturbing, mixing or shaking the solution.

FIG. 6 provides a plot showing the variance in hydrodynamic size of the AO-SPION particles produced according to the (TEA)-mediated phase transfer step of the method of FIG. 1 (Path A), when measured over time. This plot confirms that the AO-SPIONs have an ultra-high colloidal stability in water.

In order to test the quality of the presently claimed phase transfer method, the aqueous-dispersible AO-SPION particles were subjected to a rigorous testing that involved obtaining the dynamic light scattering (DLS) profile of particles over a 24 h period without disturbing the colloidal suspension of AO-SPION particles. It is noted that the hydrodynamic diameter of these AO-SPION particles remains consistent around 25 nm over this 24 hour period.

If these AO-SPION particles would have aggregated during this timeframe, the hydrodynamic diameter would have increased. Most of the nanomaterials synthesis procedure and phase-transfer methods tend to fail in this rigorous test. Therefore, researchers tend to shake the particle solution during different readings. Here, however, the colloidal solutions were not disturbed during taking of the readings over the 24 hour period, and yet the size of the particles remained the same. This provides a very strong indication that these AO-SP ION particles are ultra-stable in the aqueous phase without any potential aggregation. Such ultra-stable properties offer remarkable potential for utilizing these AO-SPIONs for biomedical and other applications, where long-term stability of the material remains an ongoing concern.

Figure 7:
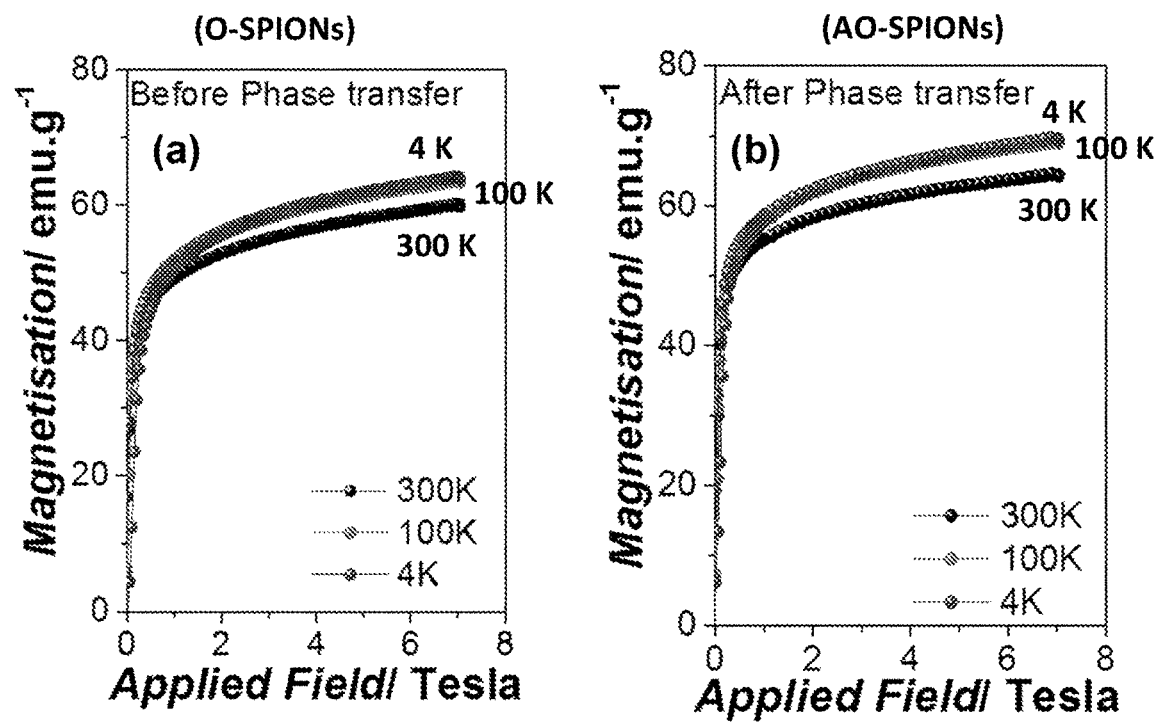
FIG. 7 provides plots comparing the magnetic properties of (a) the O-SPION particles, and (b) the AO-SPION particles produced according to the (TEA)-mediated phase transfer step of the method of FIG. 1, when measured at different temperatures (300 K, 100 K and 4 K)

FIG. 7 provides plots comparing the magnetic properties of (a) the O-SPION particles, and (b) the AO-SPION particles produced according to the (TEA)-mediated phase transfer step of the method of FIG. 1 (Path A), when measured at different temperatures (300 K, 100 K and 4 K). These measurements were performed on dry powders of particles before and after the phase transfer method.

As described in the Background section, according to literature-based protocols, the phase-transfer of particles is typically achieved by binding bulky surfactant molecules on the surface of the particles, or through growing an inorganic material such as silica on the surface of the particles. Such phase-transfer approaches degrade (reduce) the magnetic properties of materials.

Here, however, the AO-SPIONs produced by the TEA-mediated phase transfer method exhibit enhanced magnetic properties over those of the O-SPIONs. This is evident from a comparison of the spectra shown in FIGS. 7(a) and 7(b) when measured at a common temperature, where the magnetization values shown in FIG. 7(b) for the AO-SPION nanoparticles in water are higher than those shown in FIG. 7(a) for the O-SPION nanoparticles in hexane.

TABLE 1

| Sample | Blocking temperature ($T_b$) | Saturation Magnetisation (emu/g) | | |
|---|---|---|---|---|
| | | 300K | 100K | 4K |
| | Before surfactant wt. subtraction | | | |
| Before phase transfer (O-SPIONs) | ≻300K | 49.5 | 52.3 | 52.9 |
| After phase transfer (AO-SPIONs) | ≻298K | 51.5 | 55.1 | 55.5 |

The improvement in the magnetic properties described above and shown in FIG. 7 is quantitatively evident from Table 1.

Here, it is clear that irrespective of the temperature, in all the cases, the saturation magnetization is improved after phase transfer. This saturation magnetization data is for equivalent amount of iron oxide particles.

It is possible to argue that since triethylamine (TEA) is a smaller molecule than oleic acid, and since after the phase transfer method, the oleic acid molecules are potentially replaced by TEA molecules, then for the same weight amount of two materials (both with iron oxide crystals, but one in hexane coated mostly with bulky oleic acid, and the other in water mostly coated with small TEA molecules), the number of iron oxide crystals present in the two cases will be different. Essentially, based on this philosophy, for the same weight amount of material, there is likely to be less iron oxide crystals present in the O-SPION particles than those present in the aqueous soluble AO-SPION particles. Therefore, one may think that the observed improvement in the magnetic properties after the TEA-mediated phase transfer method is a potential measurement artefact.

TABLE 2

| Sample | Blocking temperature ($T_b$) | Saturation Magnetisation (emu/g) | | |
|---|---|---|---|---|
| | | 300K | 100K | 4K |
| | After surfactant wt. subtraction | | | |
| Before phase transfer (O-SPIONs) | ≻300K | 60.1 | 63.6 | 64.3 |
| After phase transfer (AO-SPIONs) | ≻300K | 64.5 | 69.3 | 69.7 |

To validate whether the magnetic properties of each iron oxide crystal improves after phase transfer, Table 2 presents the normalized data, such that the magnetization values are calculated after deducting the weight of the surfactant (or capping agent—oleic acid vs. TEA) from the original powder weight. The weight of the surfactant in each case was determined using thermo-gravimetric analysis (TGA) of these particles. It is clear that the magnetic properties of these iron oxide particles (individual single crystals) remarkably improve after phase transfer, even while considering the true weight of iron oxide, and negating the effect of any potential surface impurity. Overall, higher magnetization values are desirable for any magnetic property relevant application, such as MRI, hyperthermia, magnetic particle imaging (MPI) and the like.

The potential of these aqueous TEA mediated phase-transferred AO-SPIONs particles for magnetic resonance imaging (MRI) was assessed by calculating their relaxivity using a 9.4 Tesla Bruker Biospec MRI scanner and comparing the relaxivity values with the relaxivity values of the O-SPIONs obtained from the thermal decomposition method. The MRI phantoms revealed calculated T2 values of 196.9 mol$^{-1}$ and 238.5 mol$^{-1}$, respectively, for particles before and after phase transfer. These high T2 values indicate good ability of these iron oxide particles to cause a darkening effect during magnetic resonance imaging, and their ability to act as biomedical contrast agents. It is particularly notable that the T2 values of these O-SPION particles significantly improve after their phase-transfer to water to form AO-SPIONs, which supports the findings that the TEA-mediated phase transfer protocol offers a significant mechanism by which to enhance the performance of materials for different biomedical applications.

Figure 8:
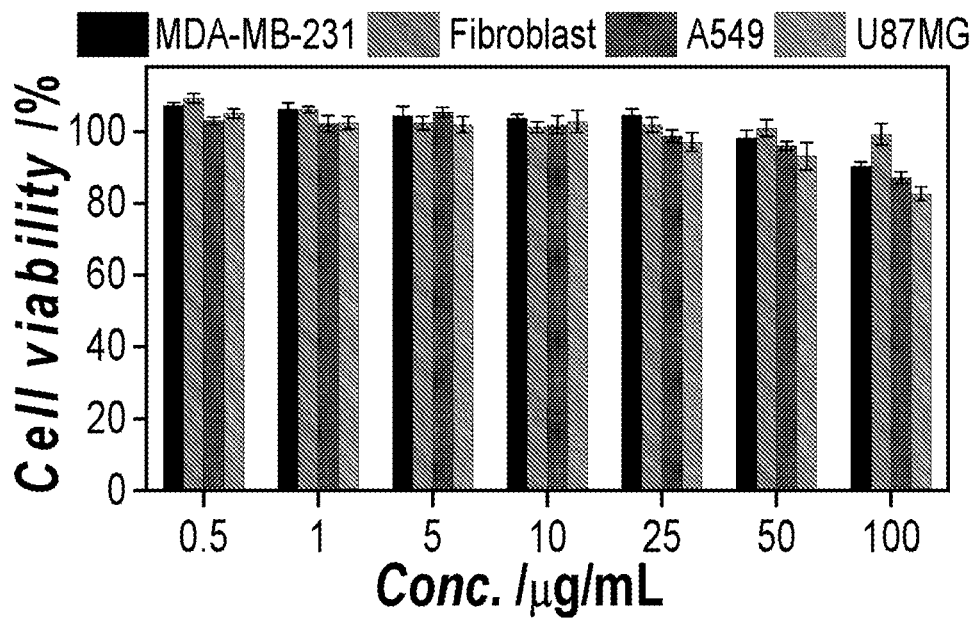
FIG. 8 provides a plot showing the biocompatibility of the AO-SPION particles produced according to the (TEA)-mediated phase transfer step of the method of FIG. 1, when assessed against a range of mammalian cells.

FIG. 8 provides a plot showing the biocompatibility of the AO-SPION particles produced according to the (TEA)-mediated phase transfer step of the method of FIG. 1 (Path A), when assessed against a range of mammalian cells.

It is clear from the results in FIG. 8 that these AO-SPION particles are biocompatible (that is, they do not cause significant cellular toxicity) as shown for the four different mammalian cell lines (MDA-MB-231, Fibroblast, A549 and U87MG) when tested for different concentration of particles. The concentrations (10, 50, 100 μg/m L) indicated in FIG. 8 are equivalent of Fe concentration (rather than the weight of iron oxide particles).

Notably, the cell viability is better than 80% even at a high 100 μg/mL Fe equivalent concentration of these particles. This is very high biocompatibility considering that it is common for Fe to start showing some toxicity at such high concentration.

Figure 9:
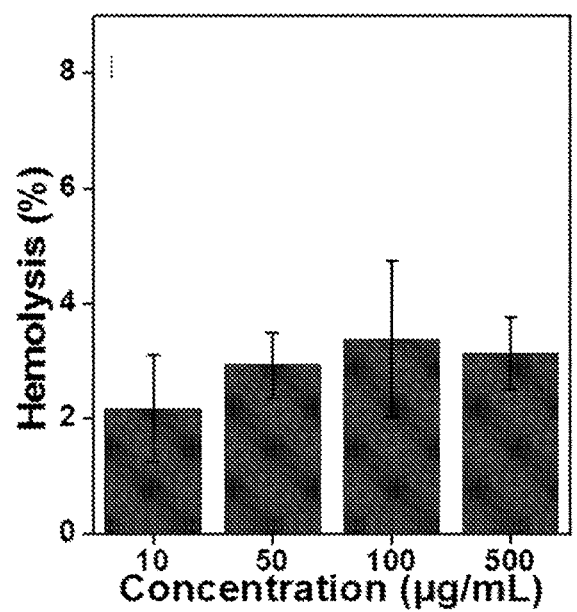
FIG. 9 provides a plot showing the hemo-compatibility of the AO-SPION particles produced according to the (TEA)-mediated phase transfer step of the method of FIG. 1, with respect to red blood cells.

FIG. 9 provides a plot showing the hemo-compatibility (with respect to red blood cells) of the AO-SPION particles produced according to the (TEA)-mediated phase transfer step of the method of FIG. 1 (Path A).

This assay involves testing the toxicity of the AO-SPION particles to highly sensitive red blood cells. Hemolysis represents the proportion of red blood cells that will be destroyed by particles. For various concentrations (10, 50, 100, 500 μg/mL) of AO-SPION particles, it is shown that the hemolysis percentages are reasonably low (between 2-4%), which further confirms the potential suitability of these particles for biomedical applications.

Materials and Methods (for Path A)

All chemicals were used as received. All chemicals and solvents were obtained from Sigma-Aldrich Australia and used without further purification.

All aqueous solutions and reagents used in the synthesis were prepared using deionized water purified using a Milli-Q™ reverse osmosis system unless otherwise stated.

Preparation of Iron Oxide Nanoparticles

Nanoparticles having a superparamagnetic iron oxide core were synthesized via a two-stage process.

In the first stage, iron oxide nanoparticles were produced by thermal decomposition according to a literature method (Park J. et al., 2004)[1], which is incorporated herein by reference. Specifically, the first stage process was carried out by synthesising an iron oleate complex by dissolving 3.24 g of iron chloride and 18.25 g of sodium oleate in a solution comprised of 40 mL ethanol, 30 mL distilled water and 70 mL hexane. Once homogenized, the solution was refluxed at 70° C. for 4 hours. Separation of the upper organic layer was carried out using a separatory funnel. Once separated, the iron oleate layer was washed twice with deionised water and separated again using a separatory funnel. Finally, the hexane was evaporated off leaving a waxy iron oleate complex. The iron oxide nanoparticles were formed by dissolving 10 g of the iron oleate complex in 1.77 g of oleic acid and 60.3 mL of 1-octadecene, followed by refluxing at 320° C. under nitrogen for 30 minutes. The resulting mixture was then allowed to cool to room temperature.

In the second stage, the iron oxide nanoparticles obtained via the thermal decomposition method were then purified using a cleaning protocol developed by the present inventors and which forms the subject of International PCT Application No. PCT/AU2017/050981 (Gammilonghi et a/.)[2], which is incorporated herein by reference. In this respect, the magnetic nanoparticles were purified by washing 1 mL of impure iron oxide nanoparticles with 49 mL of a first solvent composition comprising a 1:1 (vol/vol) ratio of diethyl ether and methanol, followed by magnetic separation of particles, and subsequent washing with 20 mL of a second solvent composition comprising a 1:1 (vol/vol) ratio of hexane and ethanol, before finally obtaining the purified iron oxide nanoparticles powder (O-SPION in Path A) by centrifugation and vacuum drying.

[Path B] and [Path C]

Figure 10:
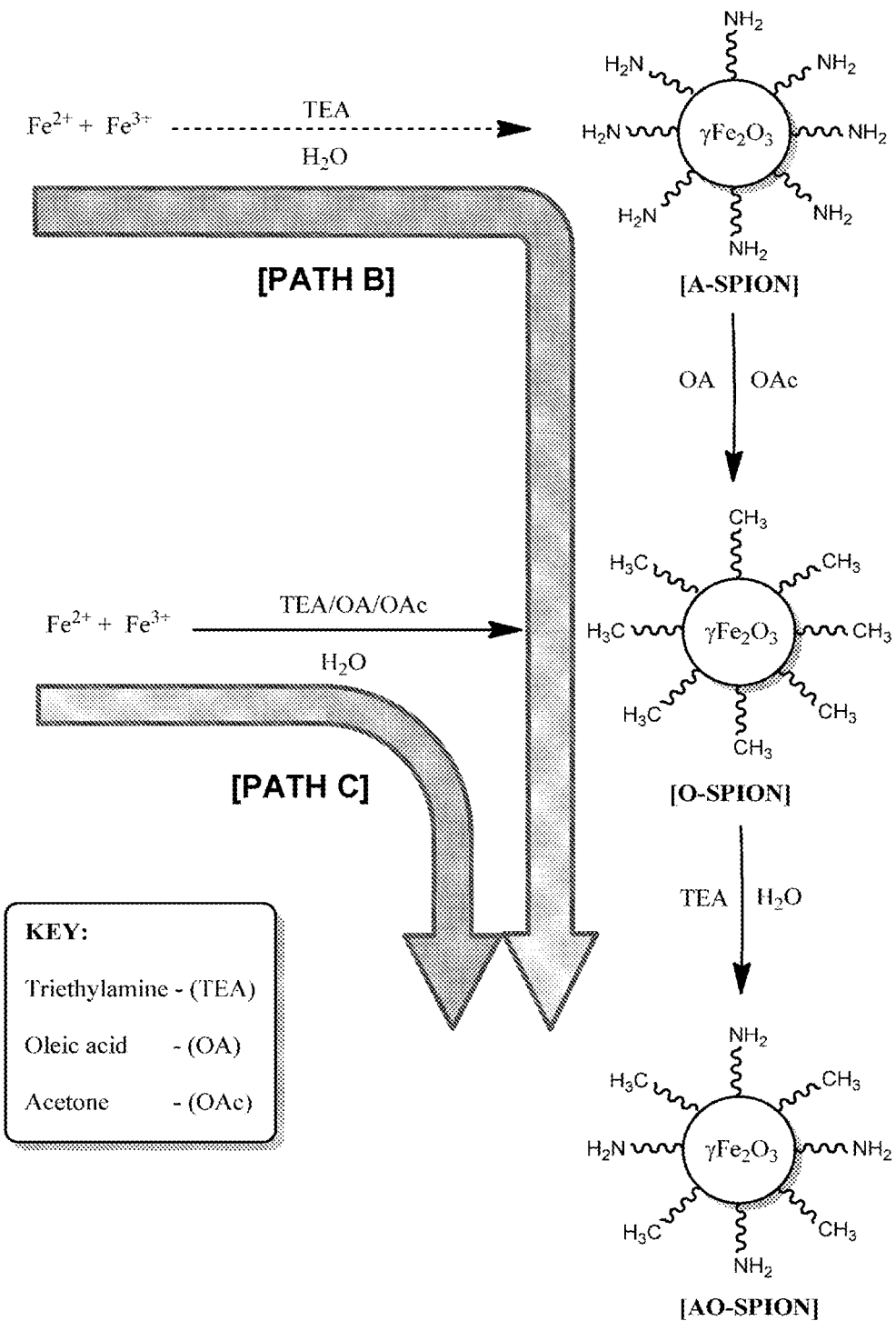
FIG. 10 shows the same schematic representation of FIG. 1, this time highlighting a second path (Path B) and a third path (Path C) to the preparation of an aqueous dispersion of SPIONs capped with both oleic acid and triethylamine ligands (AO-SPIONs)

FIG. 10 shows the same schematic representation of FIG. 1, this time highlighting a second path (Path B) and a third path (Path C) to the preparation of an aqueous dispersion of SPION particles capped with both oleic acid and triethylamine ligands (AO-SPIONs) according to another preferred embodiment of the present invention.

As will be appreciated, Path B and Path C each provide a means by which to synthesize O-SPION particles, rather than relying on the O-SPION particles pre-synthesized using the protocols provided in the literature[1,2], and as used in respect of Path A.

According to both pathways, the tertiary amine, triethylamine (TEA), is first used as a hydrolysis agent in the presence of an organic ligand, such as oleic acid in the synthesis of the O-SPION particles. Once synthesized, these O-SPION particles are then caused to undergo the same tertiary amine mediated phase transfer step highlighted in Path A to produce an aqueous dispersion of AO-SPIONs.

Method for Path B and Path C

In the case of Path B, amine-coated aqueous-dispersible iron oxide nanoparticles were first prepared in a single step according to a method described by Manna et al., Langmuir, 2018, vol. 34, 2748-2757[3], using triethylamine (TEA) as both a hydrolysing agent and a capping agent.

Specifically, when an aqueous solution containing ferric and ferrous ions in 2:1 molar ratio is exposed to TEA, the TEA promotes instantaneous hydrolysis of these iron precursors to form iron oxide nanoparticles according to equations (1) and (2):

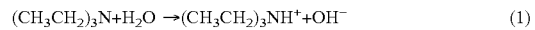
$$(CH_3CH_2)_3N + H_2O \rightarrow (CH_3CH_2)_3NH^+ + OH^- \quad (1)$$

$$Fe^{2+} + 2Fe^{3+} + 8OH^- \rightarrow Fe_3O_4 + 4H_2O \quad (2)$$

Suitably, the iron (III) ions are provided in the form of $FeCl_3 \cdot 6H_2O$ and the iron (II) ions are provided in the form of $FeCl_2 \cdot 4H_2O$.

The formed magnetite (Fe$_3$O$_4$) crystals are then further oxidised in an oxygen-rich mother solvent under ambient conditions to maghemite (γFe$_2$O$_3$), as per equation (3):

$$Fe_3O_4 + 2H^+ \gamma Fe_2O_3 + Fe^{2+} + H_2O \quad (3)$$

Here, the cationic amine molecules ((CH$_3$CH$_2$)$_3$NH$^+$, pK$_a$-10.75 for the conjugate acid in water) produced during the reaction, are simultaneously adsorbed onto the surface of the iron oxide nanoparticles via the surface hydroxyl groups, which makes them highly dispersible in the aqueous mother liqueur. These colloidal suspensions could be magnetically separated and vacuum dried in the form of a readily aqueous dispersible powder of amine-capped superparamagnetic iron oxide nanoparticles, denoted as "A-SPION" particles.

The A-SPION particles are then dispersed in an organic solution of oleic acid molecules to form a mixture, which is then agitated to form O-SPION particles. To form the organic solution, the oleic acid molecules are first dissolved in an organic solvent selected from the group consisting of acetone, methanol, ethanol, propanol, an ether, chloroform, dimethyl formamide (DMF), dimethyl sulfoxide (DMSO), and any combination thereof.

In the case of Path C, this same aqueous solution containing ferric and ferrous ions in 2:1 molar ratio is exposed to a mixture of TEA and oleic acid (OA) molecules in acetone which is then agitated to produce O-SPION particles. The agitation step is preferably conducted at a temperature that falls within a range of 70° C. to 85° C., more preferably 80° C., for a period of around 5 minutes or so.

Irrespective of which pathway is followed (Path B or Path C), the as-synthesized O-SPION particles are washed with a mixture of acetone:methanol in a 1:1 (vol/vol) ratio, and then isolated from solution by one of the physical separation procedures described above, and subsequently dried to form a powder.

Once washed, additional TEA is then used as a phase-transfer agent, to mediate the formation of the readily aqueous dispersible AO-SPION particles according to the same protocol described above in respect of Path A.

What follows is a description of one particular embodiment of the method illustrated in FIG. 10, when following Path C.

According to a first step of the method, 40 mL of an aqueous solution containing ferric (0.2 M Fe$^{3+}$) and ferrous (0.1 M Fe$^{2+}$) chloride in 2:1 molar ratio is prepared, and stirred for 5 minutes at 80° C.

According to a second step, a 5 mL acetone solution containing 0.5 mL of oleic acid molecules was added to the above solution and stirred for 2 minutes. [Note: adding oleic acid directly to the aqueous solution would have failed to mix with the water due to oleic acid being hydrophobic (oil)]. Since acetone can dissolve both oil and water, pre-mixing of oleic acid with acetone and then injecting into the aqueous solution of iron precursors allowed the formation of a homogeneous solution containing both Fe$^{2+}$ and Fe$^{3+}$ ions and oleic acid simultaneously. During this process, acetone may be replaced with any other solvent that allows high solubility of the organic ligand (oleic acid) while also offering miscibility with the aqueous phase. Examples of such solvents include acetone, ethanol, methanol, ethers, chloroform, DMF and DMSO.

According to a third step, 5 mL (amounts may vary from 0.1 to more than 5 mL) of triethylamine (TEA) was then injected into the mixed solution, enabling the instantaneous hydrolysis of the iron precursors to form oleic acid-capped superparamagnetic iron oxide nanoparticles (O-SPIONs).

The reaction was then allowed to cool under ambient conditions, accompanied with magnetic stirring. At the end of the reaction, it was found that the nanoparticles were not dispersed in the aqueous solution, but rather precipitated out at the bottom of the reaction vessel.

The obtained O-SPIONs were washed 5 times with an acetone: methanol (1:1) solution via magnetic separation and the residual solvents were evaporated overnight in an oven at 60° C. to obtain solid powders. The obtained O-SPION particles were found to disperse very well in hexane (and in other organic solvents tested), but did not disperse in water.

Characterization of Particles Prepared According to Path B or Path C

Figure 11:
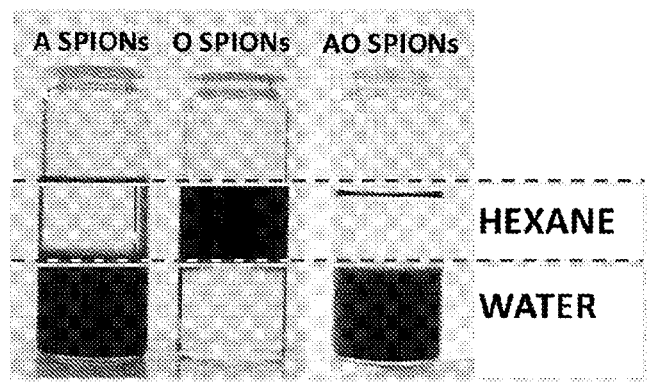
FIG. 11 shows a series of photographs comparing the solubility characteristics of powders of the SPION particles produced according to Path B and C, including SPIONs capped with (a) triethylamine ligands (A-SPIONs) from Path B, (b) oleic acid ligands (O-SPIONs) from Path C, and (c) oleic acid and triethylamine ligands (AO-SPIONs) from Path C.

FIG. 11 shows a series of photographs comparing the solubility characteristics of powders of the SPION particles produced according to Path B, in the case of SPION particles capped with (a) triethylamine ligands (A-SPIONs), and Path C in the case of SPION particles capped with (b) oleic acid ligands (O-SPIONs), and (c) oleic acid and triethylamine ligands (AO-SPIONs).

Figure 12:
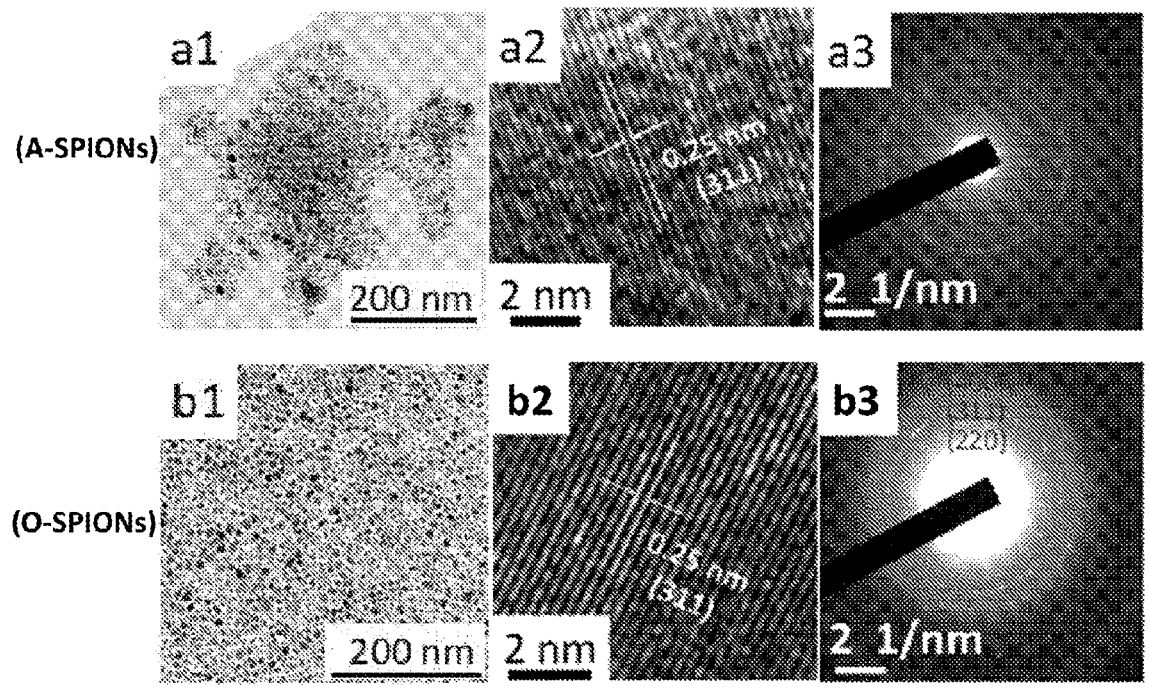
FIG. 12 shows TEM and HRTEM images along with SAED patterns of the A-SPION particles (a1-a3) and O-SPION particles (b1-b3) produced according to Path B and C, respectively.

FIG. 12 shows representative TEM and HRTEM images, along with SAED patterns, of the A-SPION particles (a1-a3) produced according to Path B and the O-SPION particles (b1-b3) produced according to Path C.

The TEM images (a1, b1) reflect particles of quasi-spherical morphology of sub-10 nm size. The corresponding HRTEM images (a2, b2) show that the obtained SPIONs are high quality single crystals of maghemite (γ-Fe$_2$O$_3$) as validated from the lattice spacing between the crystal planes.

Figure 13:
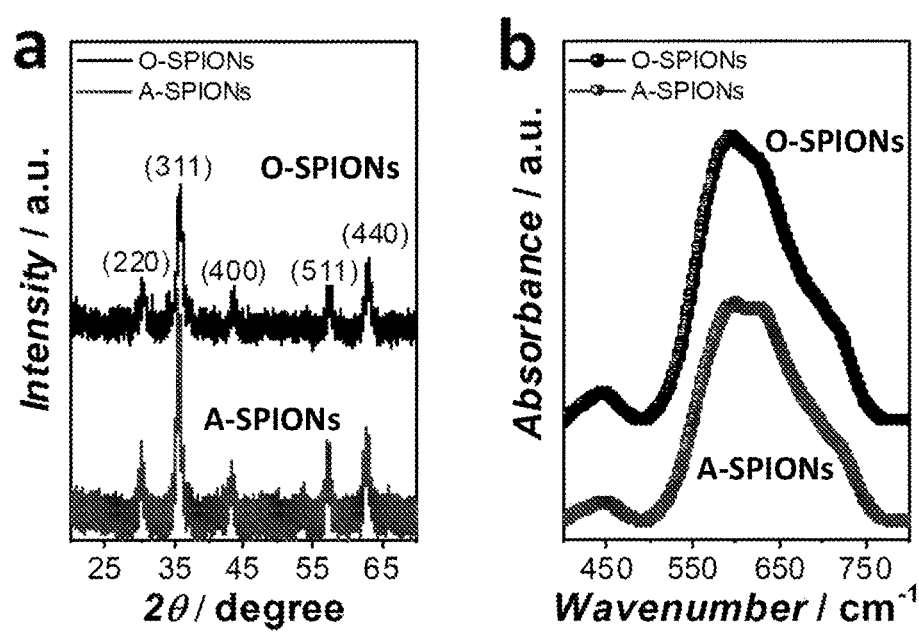
FIG. 13 provides a comparison of (a) X-ray diffraction (XRD) patterns and (b) Fourier Transform Infrared (FTIR) spectra of the A-SPION particles and 0-SP ION particles produced according to Path B and C, respectively.

FIG. 13 provides a comparison of (a) X-ray diffraction (XRD) patterns and (b) Fourier Transform Infrared (FTIR) spectra of the A-SPION particles produced according to Path B and the O-SPION particles produced according to Path C.

Specifically, the XRD patterns of the A-SPION particles and the O-SPION particles reveal the high crystallinity associated with these particles, as determined from the well-defined lattice planes and Miller indices corresponding to the γ-Fe$_2$O$_3$ phase (FIG. 13(a)).

As the similarity between the XRD patterns of maghemite (γ-Fe$_2$O$_3$) and magnetite (Fe$_3$O$_4$) does not allow reliable differentiation between these two phases, the as-produced A-SPION and O-SPION particles were characterised using Fourier Transform Infrared (FTIR) spectroscopy (FIG. 13(b)).

As shown in FIG. 13(b), in the selected region of the FTIR spectra of both the A-SPION and O-SPION particles, the broad peaks at ca. 630 cm$^{-1}$ and 448 cm$^{1-}$are characteristic of the stretching vibrations in the tetrahedral site of the Fe—O bond in γ-Fe$_2$O$_3$. This suggests that the TEA-mediated synthesis of the O-SPION particles results in the formation of a maghemite phase.

Figure 14:
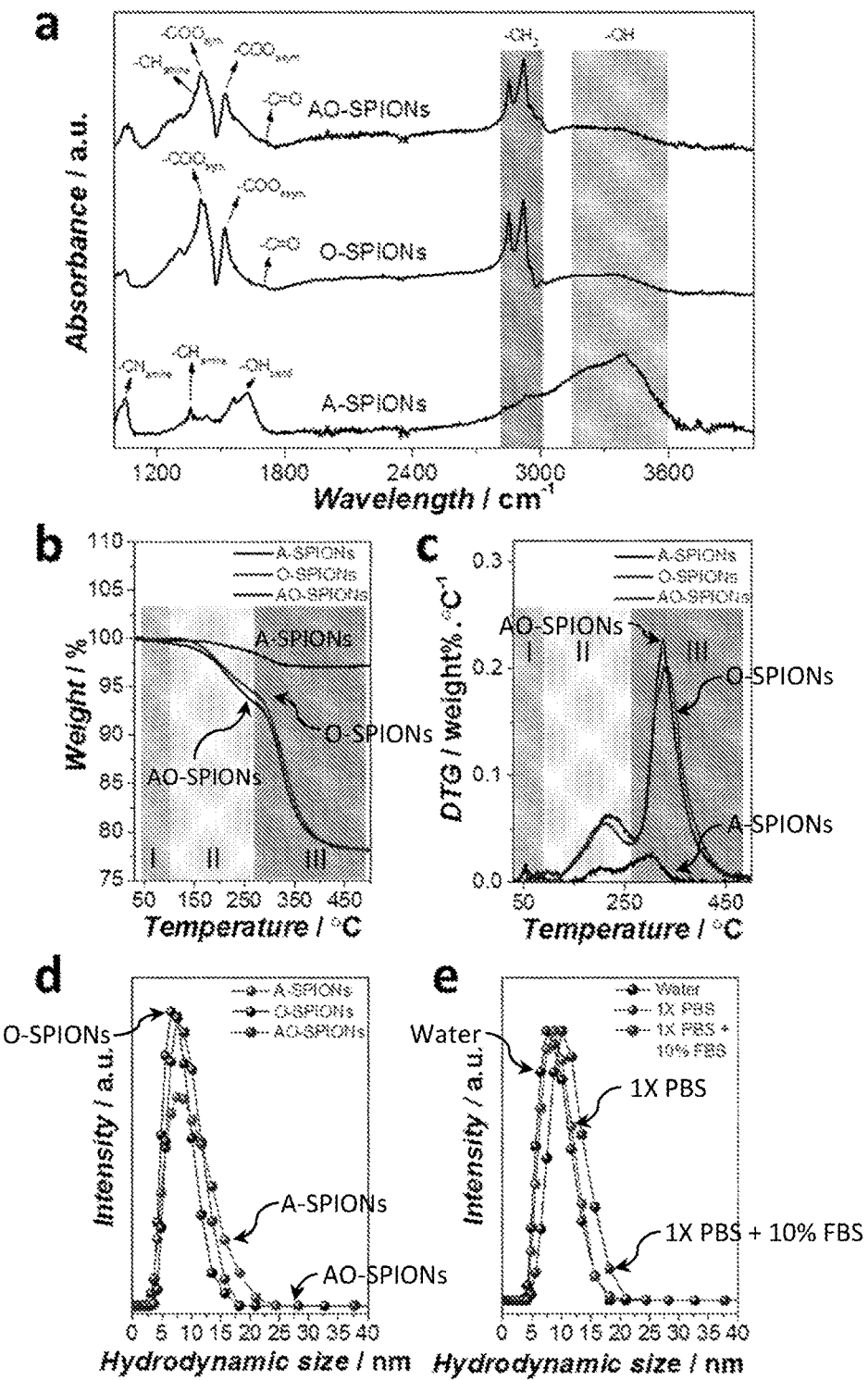
FIG. 14 provides (a) Fourier Transform Infrared (FTIR) spectra, (b) Thermogravimetric analysis (TGA), (c) Differential thermal gravimetric (DTG), (d) Dynamic light scattering (DLS) profiles of the A-SPION particles, O-SPION particles and AO-SPION particles produced according to Path B and C when measured in water, and (e) DLS profiles of the AO-SPION particles, when measured in water, 1× PBS and 1× PBS containing 10% v/v FBS.

FIG. 14 provides (a) Fourier Transform Infrared (FTIR) spectra, (b) Thermogravimetric analysis (TGA), (c) Differential thermal gravimetric (DTG), (d) Dynamic light scattering (DLS) profiles of the A-SPION particles produced according to Path B, and the O-SPION particles and AO-SPION particles produced according to Path C when measured in water, and (e) DLS profiles of the AO-SPION particles, when measured in water, 1× PBS and 1× PBS containing 10% v/v FBS.

As shown in FIG. 14(a), the wide range FTIR spectrum of the A-SPION particles reveals a strong signal corresponding to the presence of hydroxyl groups on the nanoparticle surface, as evident from the —OH vibrations at ca. 3398 and 1632 cm$^{-1}$. Additional signatures corresponding to TEA molecules are also reflected from the —CH and —CN stretching vibrations at ca. 1360 and 1057 cm$^{-1}$, respectively. Thus, the FTIR spectrum of the A-SPION particles supports the fact that the surface of these nanoparticles is rich in hydroxyl groups, and is also covered by amine (TEA) molecules, making the A-SPION particles highly dispersible in aqueous solvents.

On the other hand, in the case of the O-SPION particles, the vibrational features corresponding to the hydroxyl groups are nearly absent, and the FTIR spectrum is dominated by the vibrational modes of the oleic acid molecules that coat the surface of the particles rendering them dispersible in organic solvents. This is reflected from the —CH$_2$ stretching modes at ca. 2920 and 2851 cm$^{-1}$, along with the asymmetric and symmetric —COO stretching modes at ca. 1519 and 1408 cm$^{-1}$, respectively. The mode of interaction of the —COO groups of the oleic acid with the SPION surface can be further elucidated based on the $\Delta v_{-coo}$ (111 cm$^{-1}$) band, which is supportive of the fact that the —COO group of the oleic acid molecule binds to the nanoparticle surface via a bidentate and/or bridging coordination. Further, these oleic acid molecules form a bilayer structure onto the nanoparticle surface, as is evident from the observed free carboxylate signature at 1701 cm$^{-1}$.

Indeed, when the FTIR spectrum of the O-SPION particles is compared with that for the AO-SPION particles, the latter of which was obtained from the TEA-assisted phase transfer of O-SPIONs to water, the two FTIR spectra remain largely unchanged. For instance, in the case of the AO-SPION particles, the oleic acid molecules remain chemisorbed on the particle surface, as evident from the appearance of the —CH$_2$ stretching vibrations at 2923 and 2847 cm$^{-1}$, as well as the —COO vibrations at 1522 and 1405 cm$^{-1}$, respectively. The observed $\Delta v_{coo}$ of 117 cm$^{-1}$ also supports the notion that oleic acid remains bound to the particle surface via bidentate and/or bridging coordination as in the case of the O-SPION particles.

Further, the presence of a band associated with the C=O stretching of the free oleic acid in the case of the AO-SPION particles, supports the notion that oleic acid maintains its bilayer structure after phase transfer, suggesting that the interactions of the TEA molecules with the particle surface are not strong enough to remove the oleic acid from the particle surface.

Another notable observation is that in the TEA-mediated phase-transferred AO-SPION particles, the hydroxyl group population on the particle surface does not significantly increase. This indicates that the amphiphilicity of the TEA molecules might allow their interaction at the zone of the bilayer structure in a manner such that the hydrocarbon chains of this tertiary amine interact with the long chains of oleic acid through hydrophobic interactions, whereas their terminal amine groups provide aqueous dispersibility to these particles.

To further understand the nature of ligand binding to the nanoparticle surface, a Thermogravimetric analysis (TGA)—Differential thermal gravimetric (DTG) analysis of the SPIONs (FIG. 14(b)-(c)) was performed.

The heat-induced weight loss observed from the nanoparticle surface can be categorised into three regions, wherein region I represents the weight loss due to the removal of adsorbed moisture or surface hydroxyls; region II represents the weight loss due to loosely-bound/physisorbed ligands; and region III is broadly indicative of strongly-bound chemisorbed species. The respective weight loss values are recorded in Table 3.

TABLE 3

Percentage weight loss profile of different SPIONs as obtained from TGA-DTG

| Sample | Weight Loss (%) | | | |
| --- | --- | --- | --- | --- |
| | Region I (30-130° C.) | Region II (130-280° C.) | Region III (280-500° C.) | Total (30-500 °C.) |
| A-SPIONs | 0.23 | 1.51 | 0.83 | 2.57 |
| O-SPIONs | 0.12 | 5.91 | 16.71 | 22.74 |
| AO-SPIONs | 1.81 | 5.17 | 15.77 | 22.75 |

One of the key observations is that the A-SPION particles undergo significantly less weight loss (~2.6%) when heated over the whole temperature range in comparison to the other two SPION particles (22.7% for both O-SPIONs and AO-SPIONs). This is expected as the synthesis of the A-SPION particles involved only TEA without any oleic acid, the latter of which is a significantly larger molecule and therefore results in overall higher heat-induced weight loss in case of O-SPIONs and AO-SPIONs. Secondly, the weight loss profiles of the O-SPION particles and the AO-SPION particles are largely similar, validating the FTIR results that during phase-transfer, the TEA molecules do not undergo ligand exchange with the oleic acid molecules. As such, in the case of the A-SPION particles, the negligible weight loss observed in regions II and III is attributed to the thermal decomposition of the surface-bound TEA molecules.

Before we further discuss the TGA-DTG profile of the O-SPION particles and the AO-SPION particles, it is notable that pure oleic acid typically shows a one-step thermal decomposition at ca. 250° C., and its binding to any surface will be expected to enhance this thermal degradation temperature.

In contrast to the free oleic acid, in case of the O-SPION particles and the AO-SPION particles, a gradual two-step weight loss trend is observed in the regions of interest, wherein an initial weight loss in region II can be attributed to the decomposition of oleic acid molecules physisorbed on the surface of these SPIONs, followed by a loss in region III that corresponds to the loss of strongly chemisorbed oleic acid molecules that form a bilayer through hydrophobic interactions among the hydrocarbon chains of oleic acid.

To obtain further insights into the role of TEA as a surface ligand in these SPIONs, these materials were analysed using XPS, a highly surface-sensitive technique with a field of depth of only a few nanometres.

Figure 15:
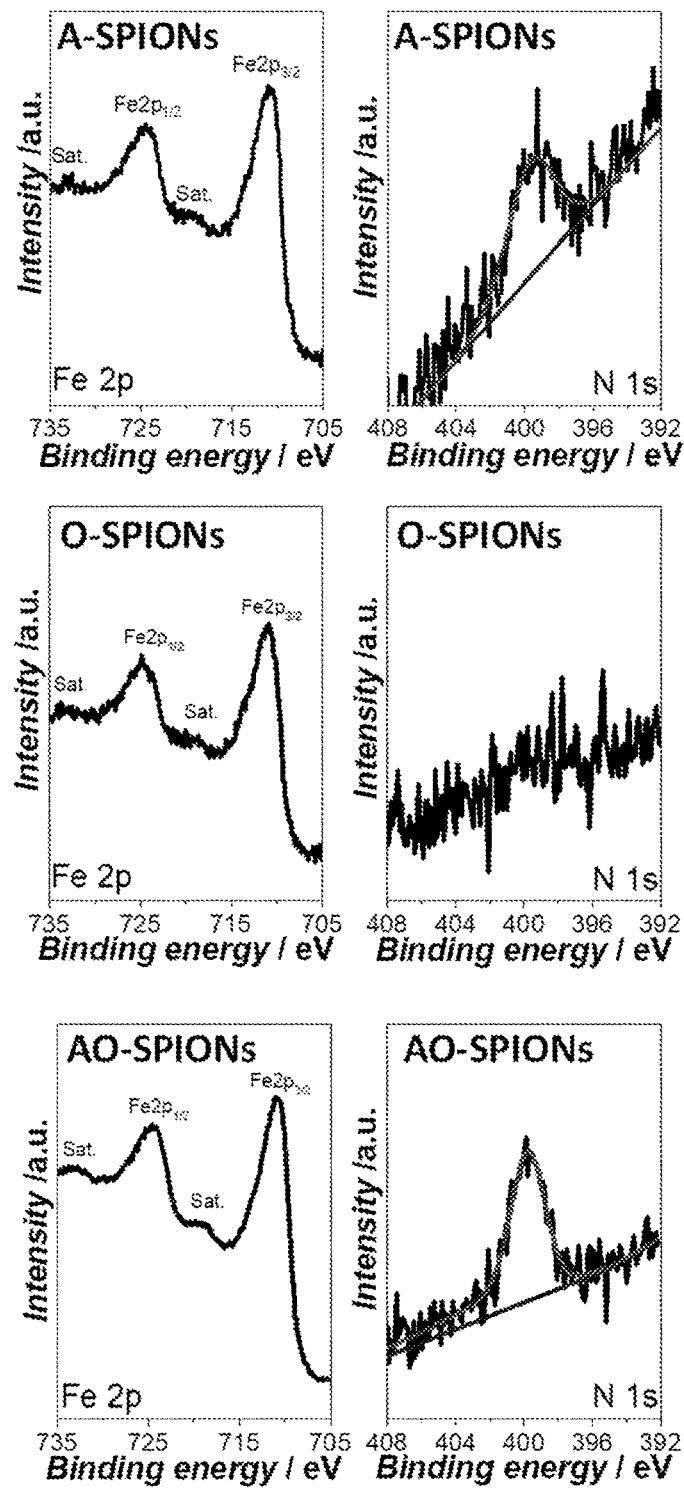
FIG. 15 provides core level X-ray photoelectron spectroscopy (XPS) spectra of the A-SPION particles, O-SPION particles and AO-SPION particles produced according to Path B and C.

Specifically, FIG. 15 provides core level X-ray photoelectron spectroscopy (XPS) spectra of the A-SPION particles produced according to Path B, and the O-SPION particles and AO-SP ION particles produced according to Path C.

The XPS analysis of all three SPIONs revealed Fe 2p$_{3/2}$ and Fe 2p$_{1/2}$ core level binding energies (BEs) at ca. 711.1 eV and 724.5 eV, respectively (with satellite peaks at higher BEs). These features are typical of Fe$^{3+}$ in maghemite, confirming the phase purity of the SPIONs. Further, the analysis of N 1s core levels revealed the presence of TEA only in the A-SPION and AO-SPION particles with BE at 399.7 eV, whereas N 1s signatures were not observed in the O-SPION particles. This supports the involvement of TEA molecules in rendering the O-SPION particles water dispersible during their TEA-mediated phase transfer to water to form the AO-SPION particles.

To understand the quality of the phase transfer step of the method, the hydrodynamic diameters of the different SPION particles were analysed using Dynamic light scattering (DLS) measurements (FIG. 14(d)) when measured in water for A-SP ION and AO-SPION particles and in hexane for O-SPION particles.

Here, the as-synthesized A-SPION and O-SPION particles revealed an average hydrodynamic radius of 8.5 and 7 nm, respectively. However, in comparison to the O-SPION particles, the A-SPION particles showed a broader particle size distribution, suggesting that the TEA-mediated synthesis of these maghemite nanoparticles in organic solvents is more desirable. This observation is not surprising, as the synthesis of iron oxide nanoparticles in organic solvents is well-known to offer higher quality crystals in comparison to those obtained in an aqueous solvent. In the current case, the ability of the TEA molecules to act as a dynamic phase transfer agent after the O-SPION particles have been synthesized in an organic solvent, offers clear advantages to obtain a high quality final product in an aqueous medium. This is evident from the comparison of the DLS spectra of the O-SPION and AO-SPION particles, suggesting that the aqueous phase transferred SPION particles retain their low polydispersity, with an average hydrodynamic diameter of 8.5 nm. Further, the ζ-potential measurements of the SPION particles in the aqueous phase revealed values of −32 mV and −46 mV for the A-SPION and AO-SPION particles, respectively, supporting the finding that the maghemite nanoparticles synthesized in the organic medium form a stable colloidal suspension after their aqueous phase transfer.

In the case of the A-SPION particles, the negative surface charge arises from the surface hydroxyl groups, whereas the negative surface charge observed for the AO-SPION particles is believed to arise from the free —COO groups present on their surface in a hydrogen-bonded environment involving the carbonyl group, triethylamine and water molecules.

For the biological applicability of these SPION particles, it is important that the particles retain their colloidal stability under physiological conditions and do not aggregate in the presence of salt and biomolecules. Typically, salts and biomolecules may neutralise the charge on the surface of nanoparticles, and therefore their presence may lead to nanoparticle aggregation, influencing their overall properties. The stability of colloids in these conditions highly depends upon the synthesis and phase transfer strategy, and high stability is critical for potential biomedical applications.

Here, since the O-SPION particles are not water-dispersible and the A-SPION particles show a relatively broad size distribution, only the AO-SPION particles with their narrow particle size distribution were subjected to stability studies under biologically-relevant conditions. This involved studying the DLS profile of the AO-SPION particles after exposing these particles independently to phosphate buffer saline (1× PBS) that mimics the physiological osmolarity, and to a mixture containing 1× PBS with 10% foetal bovine serum (1× PBS +10% v/v FBS) that represents the serum proteins present in the biological fluids (FIG. 14(e)). The hydrodynamic size provides information about the effective hydrated size of the particles in a solution. If the particle aggregation occurs, this would result in a significant broadening and associated increase in the hydrodynamic size. In contrast, if biomolecules in the surrounding solution interact with the particles and form a biomolecular corona, this will appear as slight increase in the hydrodynamic size.

As evident from FIG. 14(e), the average hydrodynamic radius of the AO-SPION particles dispersed in water (8.5 nm) does not significantly change in the presence of 1× PBS (8.9 nm), but slightly increases in the presence of additional FBS (10.6 nm). It is however notable that the presence of FBS does not significantly affect the particle size distribution, and therefore this increase in hydrodynamic diameter can be attributed to the formation of a serum protein corona on the particle surface. These results clearly demonstrate the high stability of the AO-SPION particles produced following the TEA-mediated phase transfer step of the method and support the potential usage of these AO-SPION particles for biomedical applications.

Next, the magnetic properties of the A-SPION particles, 0-SP ION particles, and AO-SPION particles were studied by measuring the temperature-dependent (M-T) and field-dependent (M-H) magnetisation curves.

Figure 16:
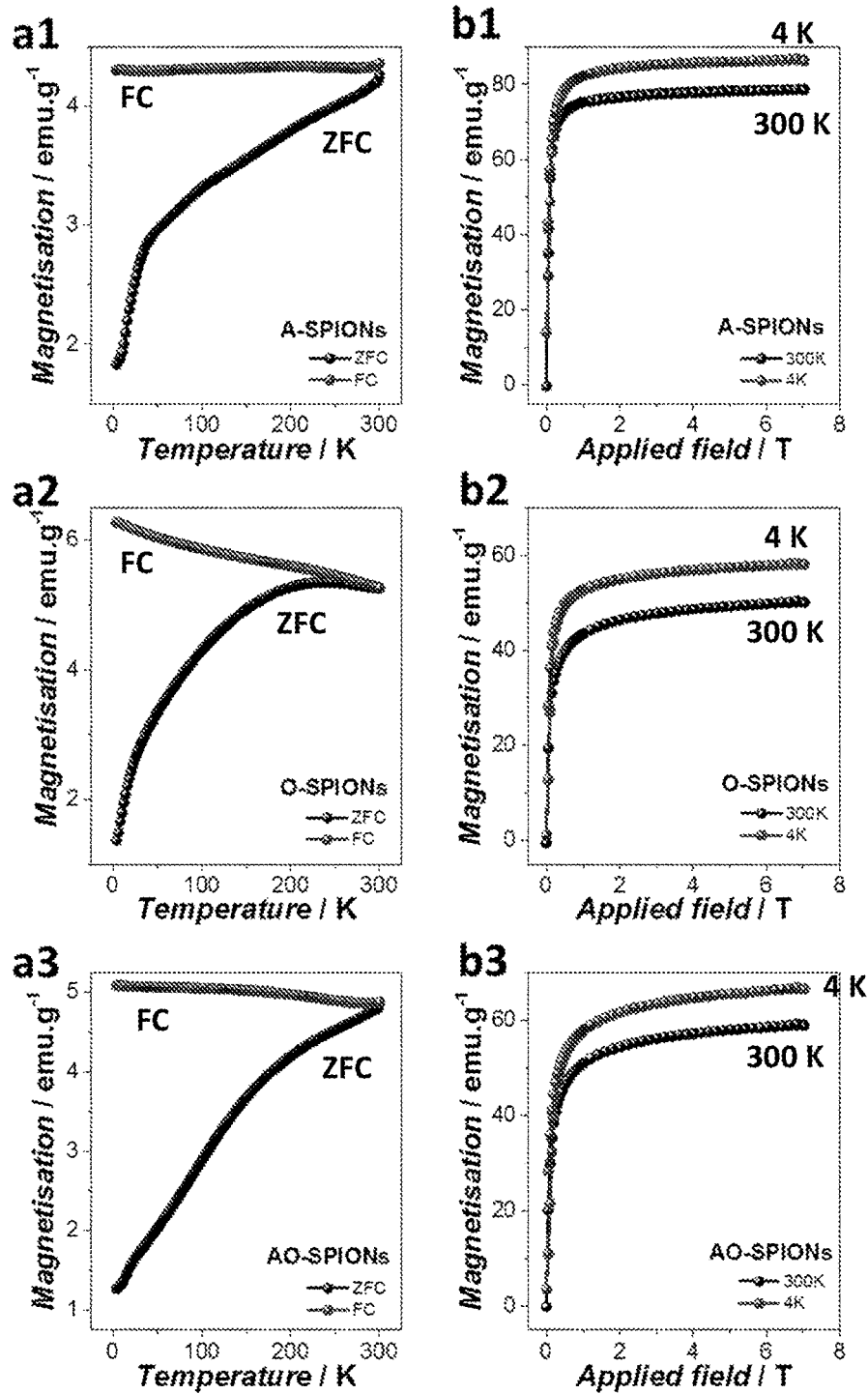
FIG. 16 provides temperature-dependent (M-T) (a1-a3) and field-dependent (M-H) (b1-b3) magnetisation curves showing the magnetic properties of the A-SP ION particles, O-SPION particles and AO-SPION particles produced according to Path B and C.

FIG. 16 provides temperature-dependent (M-T) (a1-a3) and field-dependent (M-H) (b1-b3) magnetisation curves showing the magnetic properties of the A-SP ION particles produced according to Path B, and the O-SPION particles and AO-SPION particles produced according to Path C.

As shown in FIG. 16, in all three cases, the M-T curves reveal that the ZFC (zero filed cooled) magnetisation monotonically increases with an increase in temperature when compared to the FC (field cooled) magnetisation (FIG. 16(a)). In all these cases, the ZFC and FC curves overlap at or above the room temperature (blocking temperature-$T_b$), supporting the room-temperature super-paramagnetism in these SPION particles.

The superparamagnetic behaviour is also revealed from the M-H curves that show higher saturation magnetisation (Ms) at lower temperature (4 K) compared to that at 300 K (FIG. 16(b) and Table 4).

TABLE 4

Saturation magnetization (Ms) values of different SPIONs as function of temperature.

| | Saturation Magnetisation (emu/g equivalent of iron oxide particles) | | |
|---|---|---|---|
| Sample | 300K | 100K | 4K |
| A-SPIONs | 78.7 | 86.0 | 86.8 |
| O-SPIONs | 50.2 | 57.3 | 58.4 |
| AO-SPIONs | 59.3 | 66.2 | 67.0 |

The A-SPION particles, O-SPION particles and AO-SPION particles showed the room-temperature Ms values of 78.7, 50.2 and 59.3 emu/g, respectively. High Ms values correspond to high relaxivities, and are desirable for different biomedical applications, ranging from MRI to hyperthermia. As such, the values obtained in the current case are on the higher end of bulk saturation magnetisation typically observed for maghemite nanoparticles. Higher Ms is expected from the A-SPION particles compared to the O-SPION particles and the AO-SPION particles due to the lack of the bulky oleic acid molecules on the surface of the A-SPION particles. Another notable observation is the ~20% increase in the Ms of AO-SPIONs once the O-SPION particles have been phase-transferred to water (Table 4). Considering that the FTIR, TGA-DTG and XPS data did not support a ligand exchange mechanism, this increase in saturation magnetisation might be attributed to a number of other factors such as surface spin canting or frustration of anti-ferrimagnetic exchange interactions, whose effect becomes more pronounced when the particle size decreases.

Hyperthermia

Few studies have been made to date where similar nanoparticles with the same composition and particle size distribution in both aqueous and non-aqueous media have been evaluated for their hyperthermia performance. This is a rather important parameter, as the surrounding medium plays a great role while evaluating the field-dependent heating ability of SPION particles.

The TEA-mediated synthesis and phase-transfer protocol reported here enables one to make this direct comparison by evaluating the properties of these SPION particles as heat susceptors for radiofrequency (RF)-induced heating.

Figure 17:
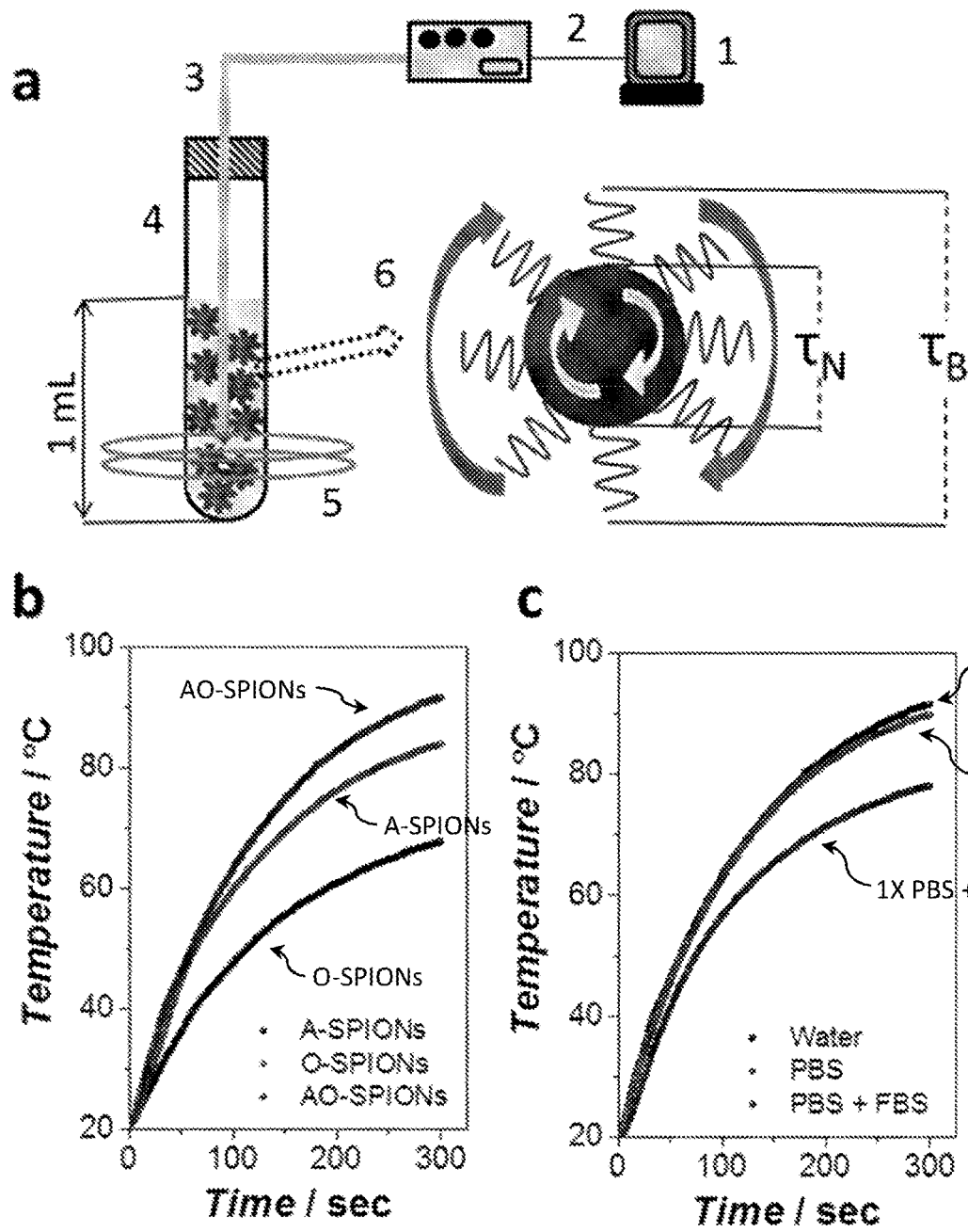
FIG. 17 shows (a) a schematic representation of a magnetic hyperthermia unit for use in testing the magnetic hyperthermia response of the SPION particles, (b) a plot of the magnetic hyperthermia response of of the A-SPION particles produced according to Path B, and O-SPION particles and AO-SPION particles produced according to Path C, as a function of time on exposure to a fixed AC magnetic field of 400 kHz, as evaluated from change in the temperature of the dispersion media [water in the case of A-SPIONs and AO-SPIONs, toluene in the case of O-SPIONs], and (c) a plot that compares the hyperthermia performance of AO-SPION particles, when conducted in water, 1× PBS and 1× PBS +10% FBS to mimic a biological scenario.

To investigate the heating abilities of these SPIONs for potential hyperthermia application, a fixed iron equivalent concentration was chosen to minimize the effects of magnetic field inhomogeneities, and measurements were performed using the set up shown in FIG. 17(a).

Briefly, FIG. 17(a) shows a schematic representation of a magnetic hyperthermia unit for use in testing the hyperthermia response of the A-SPION particles produced according to Path B, and the O-SPION particles and AO-SPION particles produced according to Path C.

Specifically, as shown in FIG. 17(a), the magnetic hyperthermia unit includes (1) a computer to record the change in temperature with a 1 s resolution, (2) a temperature base controller, (3) a fibre optics-based thermometer, (4) a sample holder, (5) a water-cooled two coil copper rings attached to an AC generator (400 kHz), and (6) a representative SPION with indicated Néel ($T_B$) and Brownian ($T_B$) relaxations.

FIG. 17(b) shows a plot of the magnetic hyperthermia response of the A-SPION particles produced according to Path B, and the O-SPION particles and AO-SPION particles produced according to Path C, as a function of time on exposure to a fixed AC magnetic field of 400 kHz, as evaluated from change in the temperature of the dispersion media [water in the case of A-SPIONs and AO-SP IONs, toluene in the case of O-SPIONs].

For hyperthermia measurements, the A-SPION and AO-SPION particles were directly suspended in water, while the O-SPION particles were suspended in toluene as the solvent affords a high boiling point of 110.6° C. to perform hyperthermia measurements. To remove the influence of external thermal gradients, the two-turn copper coil (5) was cooled with circulating cold water and the sample was placed in sample holder (4) in the form of a plastic vial covered with thick polystyrene foam insulation, achieving near adiabatic conditions. After switching on the RF source (400 or 200 kHz frequency with a field amplitude of 10 kA.m$^{-1}$), temperatures were recorded using the thermometer (3) every 1 s for a total span of 300 s.

To keep the current study relevant to biological hyperthermia, the RF parameters chosen were at 400 kHz and lower frequencies, which are considered biologically safe. It has been noted that at 400 kHz, the field penetration into tissues at 15 cm depth is more than 99%, whereas the background non-specific heating of surrounding water and tissues due to eddy currents remains insignificant in the 350-400 kHz frequency range. In vivo studies have also shown that the AC field of 500 kHz with amplitude of 37.3 kA.m$^{-1}$ does not cause any negative health impact on animals during magnetic hyperthermia. These prior observations suggest that our RF parameters are relevant to the safe operational limits of the biomedical hyperthermia.

The specific absorption rates (SAR) obtained from the linear regression analysis of time-dependent temperature increase profile of different SPIONs at 400 kHz reveal the SAR values of 96.9 W.g$^{-1}$ for the A-SPION particles and 65.3 W.g$^{-1}$ for the O-SPION particles (FIG. 17(b)), calculations are detailed in the Materials and Method section which follows, and the specific absorption rates (SAR) under different conditions are summarised in Table 5.

TABLE 5

SAR values (W · g$^{-1}$) of different SPIONs under different conditions.

| Sample | 400 kHz | | | 200 kHz |
| --- | --- | --- | --- | --- |
| | Water/Toluene | 1X PBS | 1X PBS + 10% FBS | Water/Toluene |
| A-SPIONs | 96.9 | — | — | 52.1 |
| O-SPIONs | 65.3 | — | — | 31.0 |
| AO-SPIONs | 139.9 | 131.7 | 110.8 | 84.4 |

This ~50% higher SAR value for the A-SPION particles is consistent with the relative saturation magnetisation of these materials, in which case the A-SPION particles showed ~50% higher Ms over the O-SPION particles. Interestingly, when the O-SPION particles are phase transferred to water, the SAR value for the resultant AO-SPION particles is enhanced by 45% to 139.9 W.g$^{-1}$. This remarkable SAR enhancement can be understood based on two major contributory factors responsible for magnetic field-induced heating. These include (i) Néel ($T_N$) relaxation that involves change in the orientation of the inherent magnetisation of a SPION, and (ii) Brownian relaxation ($T_B$) that involves the rotation of the SPION with respect to the surrounding dispersion medium under an applied magnetic field. Since the inorganic component (composition, crystal structure, size, polydispersity) of the O-SPION and AO-SPION particles is exactly the same, the contribution of the Neel ($T_N$) relaxation to the magnetic hyperthermia may be safely considered equivalent in both cases. Therefore, it is the change in the nature of the Brownian relaxation ($T_B$) that seems to play a significant role in enhancing the SAR value for the phase-transferred AO-SPION particles. Additional SAR measurements at lower frequency (200 kHz) reveal approximately 50% reduction in the SAR values (Table 5), which is expected considering the linear relationship between the SAR and applied frequency.

In addition, since the AO-SPION particles reveal a narrow particle size distribution and high stability under different physiologically-relevant conditions (FIG. 14(e)), the SAR activity of the AO-SPION particles dispersed in water was compared with those after dispersion in either 1× PBS or in 1× PBS along with 10% FBS (FIG. 17(c)). The SAR activity of these particles only reduced marginally and they continue to show high SAR activity, which can be attributed to the high stability of these phase-transferred particles in the present of salts and serum.

Overall, these observations reflect upon the importance of a suitable phase transfer protocol employed for transferring high quality iron oxide nanocrystals to an aqueous phase. As such, in the current case, TEA acts as a dynamic ligand that not only allows direct synthesis of iron oxide nanocrystals both in aqueous and organic solvents, but also facilitates phase transfer of nanoparticles synthesised in organic medium to an aqueous medium while ensuring that the end product is suitable for hyperthermia applications.

The various embodiments of the present invention rely on the use of triethylamine as a dynamic molecule to produce superparamagnetic iron oxide nanocrystals of maghemite phase capped with both hydrophobic ligands and triethylamine ligands that are readily dispersible both in aqueous and organic environments. In particular, it is observed that the triethylamine facilitates the phase-transfer of the hydrophobic oleic acid-capped SPION particles (O-SPIONs) from the non-aqueous phase to the aqueous phase in a single step. This new phase transfer protocol is not only rapid and highly efficient, it is also apparent that the magnetic properties of the resultant SPION particles capped with both oleic acid and triethylamine molecules (AO-SPIONs) were found to improve after transfer to the aqueous phase. This is rarely the case, as existing phase transfer protocols typically deteriorate the magnetic properties of such O-SPIONs.

These phase-transferred AO-SPION particles demonstrate outstanding magnetic properties which could be exploited for a proof-of-concept demonstration in magnetic hyperthermia. While the materials reported in this study are likely to find use in biomedical applications, it is important to highlight the versatility of TEA molecules as unique amphiphilic tertiary molecules for a variety of applications.

In addition to magnetic hyperthermia, the readily aqueous dispersible AO-SPION particles are anticipated to find use in other applications that rely on the magnetic properties of these SPIONs. For instance, such magnetism-mediated applications may include, but not limited to: magnetic labelling, magnetic separation, magnetism-directed targeting, magnetic resonance imaging, magnetic particle imaging and magnetism-induced heating.

Materials and Methods (for Path B and Path C)

Materials: Iron (III) chloride hexahydrate ($FeCl_3 \cdot 6H_2O$), iron (II) chloride tetrahydrate ($FeCl_2 \cdot 4H_2O$), oleic acid (90% purity), toluene, triethylamine (99% purity), phosphate buffer saline (PBS), foetal bovine serum (FBS), acetone and methanol were all purchased from Sigma-Aldrich and used as received. Deionised Milli-Q water was used in all of the experiments.

Nanoparticle synthesis: A-SPION synthesis—A 40 mL of aqueous solution containing ferric (0.2 M $Fe^{3+}$) and ferrous (0.1 M $Fe^{2+}$) ions in 2:1 molar ratio was stirred for 5 minutes in an oil bath at 80° C. under ambient environment. This was followed by rapid injection of 5 mL of TEA into the solution, enabling the hydrolysis of iron precursors to form iron oxide nanoparticles. The reaction products were then allowed to cool under ambient conditions over one hour, accompanied with magnetic stirring. The obtained nanoparticles were washed 5 times with acetone: methanol (1:1) solution via magnetic separation and the residual solvents were evaporated overnight in an oven at 60° C.

O-SPION synthesis—The synthesis protocol is largely similar to that of the A-SPIONs except that before injecting the TEA into the aqueous solution containing ferric ($Fe^{3+}$) and ferrous ($Fe^{2+}$) ions, a 5 mL of acetone solution containing 0.5 mL of oleic acid was added to iron precursors and stirred for 2 min.

Nanoparticle phase transfer: AO-SPION synthesis—The O-SPIONs synthesized using the approach mentioned in the earlier section served as the starting material. 1 mL of TEA was added to 0.1 g of the O-SPIONs powder, and sonicated for 1 min using a standard bench-top sonicator (Unisonics FXP4M with operating power of 40 W).

Excess TEA and oleic acid ligands were removed by dialysis in the presence of excess water over a 24 hour period using a 12 kDa cut-off dialysis membrane with four changes of water. An appropriate amount of water can be added to prepare aqueous-dispersible AO-SPION particles of a pre-defined nanoparticle concentration.

Material characterization: The particle size and size distribution were evaluated from transmission electron microscopy (TEM) images, which were obtained using the JEOL 1010 TEM instrument operated at 100 kV. TEM was also employed to obtain the corresponding selected area electron diffraction (SAED) patterns of nanoparticles. High resolution TEM (HRTEM) images were obtained using JEOL 2100F microscope operated at 80 kV.

Thermogravimetric analysis (TGA-DTG) was performed to quantify the extent of oleic acid coating using a Pyris 1 TGA instrument (Perkin-Elmer, Inc.) with a ramping rate of 5° C. min$^{-1}$ in the temperature range of 30-600° C. under an inert ($N_2$) atmosphere.

X-ray diffraction (XRD) and Fourier transform infrared spectroscopy (FTIR) studies were performed to determine the iron oxide phase and the surface chemistry of the nanoparticle surface. XRD patterns were recorded using a Bruker AXS D4 Endeavor Wide Angle X-Ray Diffraction instrument with CuKa radiation ($\lambda$: 1.5406 Å) at room temperature.

FTIR spectra of the nanoparticles were collected using a Perkin Elmer spectrum 100 spectrometer in the range of 4000-400 cm$^{-1}$ at 4 cm$^{-1}$ resolution. All presented spectra are the average of 256 scans.

For X-ray photoemission spectroscopy (XPS), samples were prepared by drop casting the sample on Si substrates coated with a 100nm thermally-evaporated Au thin film, and measurements were carried out using a Thermo Scientific K-Alpha XPS instrument using an AlKa X-ray source (1486.7 eV) at a pressure better than 1×10$^{-9}$ Torr (1 Torr=1.333×10$^2$ Pa). The general scan and $C_{1s}$, $Fe_{2p}$, $Si_{2p}$, $O_{1s}$, and $N_{1s}$ core level spectra for the samples were recorded with an un-monochromatized MgKa radiation (photon energy of 1253.6 eV) at a pass energy of 20 eV and an electron take off angle of 90°. The overall resolution was 0.1 eV for XPS measurements. The core level spectra were background corrected using a Shirley algorithm and chemically distinct species were resolved using standard Gaussian-Lorentzian functions.

The core level binding energies (BE) were aligned with adventitious carbon binding energy of 285 eV. Hydrodynamic size of the nanoparticles was obtained from the dynamic light scattering (DLS) measurements using a Malvern Zetasizer.

A Superconducting Quantum Interference Device (SQUID) magnetometer MPMS-XL (Quantum Design, USA) was used for characterising the magnetic properties. For the zero-field cooled (ZFC) measurements, the sample was cooled at 4 K in the absence of an external magnetic field. A field of 100 Oe was then applied and the magnetisation was measured with increasing temperature. For the field-cooled (FC) measurement, the sample was cooled at 4 K in the presence of a 100 Oe field and then the magnetisation was measured with increasing temperature. The field-dependent magnetisation was measured at 300 K, 100 K and 4 K. The measured magnetisations were normalised with respect to the net mass of iron oxide, i.e. deducing the weight of the surfactant (determined by TGA-DTG).

Hyperthermia measurements: The heating properties of the nanoparticle were measured within the span of 300 seconds by using a 400 kHz generator with nominal power output of 2.5 kW and the rise in temperature was measured with respect to time. The ability of the nanoparticles to dissipate the heat under the alternating magnetic field via the Brownian ($T_B$) and Neel ($T_N$) relaxation mechanisms were measured in terms of specific absorption rate (SAR) using the formula:

$$SAR = \frac{m_L c_{p,L} + m_{NP} c_{p,NP}}{m_{NP}} \frac{\Delta T}{\Delta t} = \frac{c_p}{w_{NP}} \frac{\Delta T}{\Delta t} \tag{4}$$

where ΔT is change in temperature, Δt is change in time, ΔT/Δt is the heating rate of the colloidal dispersions of iron oxide nanoparticles, as evaluated from the linear section of the temperature rise curve; $w_{Np}$ is the mass fraction of iron oxide nanoparticles in the sample; and $c_p$ is the mean value of its specific heat capacity in the investigated temperature range.

REFERENCES

[1] Park, J., et al., *Nature Materials*, 2004, vol. 3, 891-895.

[2] International PCT Patent Application No. PCT/AU2017/050981 (Gammilonghi et al.).

[3] Manna et al., *Langmuir*, 2018, vol. 34, 2748-2757

Definitions

Whenever a range is given in the specification, for example, a temperature range, a time range, or concentration range, all intermediate ranges and subranges, as well as all individual values included in the ranges given are intended to be included in the disclosure. It will be understood that any subranges or individual values in a range or subrange that are included in the description herein can be excluded from the claims herein.

All definitions, as defined and used herein, should be understood to control over dictionary definitions, definitions in documents incorporated by reference, and/or ordinary meanings of the defined terms.

Throughout this application, the term "about" is used to indicate that a value includes the inherent variation of error for the device, the method being employed to determine the value, or the variation that exists among the study subjects.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The term "mixture" as used herein in the specification, should be understood to encompass not only solutions having components (e.g., phases, moieties, solvents, solutes, molecules, and the like) that are homogenously mixed together, but also combinations of components or materials that are not necessarily evenly, homogeneously, or regularly distributed when combined (e.g., unevenly mixed combinations of components, separated layers of immiscible components, unevenly distributed suspensions, and the like).

Spatially relative terms, such as "inner," "outer," "beneath," "below," "lower," "above," "upper," and the like, may be used herein for ease of description to describe one element or feature's relationship to another element(s) or feature(s) as illustrated in the Figures. Spatially relative terms may be intended to encompass different orientations of the device in use or operation in addition to the orientation depicted in the Figures.

While the invention has been described in conjunction with a limited number of embodiments, it will be appreciated by those skilled in the art that many alternatives, modifications and variations in light of the foregoing description are possible. Accordingly, the present invention is intended to embrace all such alternatives, modifications and variations as may fall within the spirit and scope of the invention as disclosed.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

The present application may be used as a basis or priority in respect of one or more future applications and the claims of any such future application may be directed to any one feature or combination of features that are described in the present application. Any such future application may include one or more of the following claims, which are given by way of example and are non-limiting in regard to what may be claimed in any future application.

The invention claimed is:

1. A method for preparing an aqueous dispersion of metal oxide particles, comprising the step of:
performing phase transfer of a plurality of metal oxide particles capped with hydrophobic ligands on a surface there of by contacting the metal oxide particles with a combination of tertiary amine and water to form a biphasic mixture, and agitating said biphasic mixture to produce an aqueous dispersion of metal oxide particles capped with hydrophobic ligands and tertiary amine ligands on the surface thereof.

2. A method according to claim 1, wherein the biphasic mixture is agitated by sonicating the biphasic mixture for greater than 5 minutes.

3. A method according to claim 1, wherein prior to the phase transfer step, the method further comprises the step of:
dissolving the tertiary amine in a solvent to form a solution of the tertiary amine;
wherein the solvent is a non-polar solvent selected from the group consisting of hexane, toluene and a combination thereof;
or wherein the solvent is a polar solvent selected from the group consisting of water, methanol, ethanol, propanol, an ether, chloroform, dimethyl formamide (DMF), dimethyl sulfoxide (DMSO), and any combination thereof.

4. A method according to claim 1, further comprising the step of:
separating the metal oxide particles capped with hydrophobic ligands and tertiary amine ligands on the surface thereof from the aqueous dispersion using a physical separation procedure.

5. A method according to claim 1, wherein the metal oxide particles capped with hydrophobic ligands and tertiary amine ligands are separated from the biphasic mixture by centrifuging the biphasic mixture at greater than 1000 g for greater than 2 minutes.

6. A method according to claim 1, wherein the plurality of metal oxide particles are iron oxide particles, and prior to the phase transfer step of, the method further comprises the step of:
contacting an aqueous solution of iron (III) and iron (II) ions with a tertiary amine and hydrophobic ligands dissolved in an organic solvent to facilitate hydrolysis of the iron (III) and iron (II) ions to produce an organic dispersion of iron oxide particles capped with hydrophobic ligands on the surface thereof.

7. A method according to claim 6, wherein the iron (III) and iron (II) ions are present in the aqueous solution in a 2:1 molar ratio.

8. A method according to claim 6, wherein the organic solvent is miscible with the aqueous solution.

9. A method according to claim 8, wherein the organic solvent is acetone.

10. A method according to claim 1, wherein the tertiary amine is a trialkylamine.

11. A method according to claim 10, wherein the trialkylamine is selected from the group consisting of triethylamine and trimethylamine.

12. A method according to claim 10, wherein the tertiary amine is triethyiamine.

13. A method according to claim 1, wherein the hydrophobic ligands are selected from the group consisting of an alkanoic acid, a saturated or unsaturated fatty acid, or a combination thereof.

14. A method according to claim 13, wherein the hydrophobic ligands are oleic acid.

15. A method according to claim 1, wherein the metal oxide particles are iron oxide particles.

16. A method according to claim 15, wherein the iron oxide particles are maghemite ($\gamma$-$Fe_2O_3$) and/or magnetite ($Fe_3O_4$).

17. A method of using an aqueous dispersion of metal oxide particles produced according to the method of claim 1 as magnetic particles in a magnetism-mediated process selected from the group of processes consisting of magnetic hyperthermia treatment, magnetic labelling, magnetic separation, magnetic resonance imaging, magnetic particle imaging, magnetism-directed targeting and magnetism-induced heating.

18. A composition for use in a magnetism-mediated process comprising an aqueous dispersion of metal oxide particles produced according to the method of claim 1, the magnetism-mediated process selected from the group of processes consisting of magnetic hyperthermia treatment, magnetic labelling, magnetic separation, magnetic resonance imaging, magnetic particle imaging, magnetism-directed targeting and magnetism-induced heating.

* * * * *